United States Patent [19]

Kawagishi et al.

[11] Patent Number: 4,585,732

[45] Date of Patent: * Apr. 29, 1986

[54] SILVER HALIDE PHOTOGRAPHIC LIGHT-SENSITIVE MATERIAL

[75] Inventors: Toshio Kawagishi; Nobuo Furutachi, both of Kanagawa, Japan

[73] Assignee: Fuji Photo Film Co., Ltd., Kanagawa, Japan

[*] Notice: The portion of the term of this patent subsequent to Feb. 19, 2002 has been disclaimed.

[21] Appl. No.: 686,955

[22] Filed: Dec. 27, 1984

[30] Foreign Application Priority Data

Dec. 27, 1983 [JP] Japan ................................ 58-250345

[51] Int. Cl.$^4$ ............................................... G03C 7/26
[52] U.S. Cl. ................................... 430/558; 430/387; 430/505; 430/548
[58] Field of Search ............... 430/558, 548, 387, 505

[56] References Cited

U.S. PATENT DOCUMENTS

| | | | |
|---|---|---|---|
| 3,725,067 | 4/1973 | Bailey et al. | 430/558 |
| 4,083,721 | 4/1978 | Inouye et al. | 430/558 |
| 4,500,630 | 2/1985 | Sato et al. | 430/558 |
| 4,503,141 | 3/1985 | Furutachi et al. | 430/558 |

Primary Examiner—J. Travis Brown
Attorney, Agent, or Firm—Sughrue, Mion, Zinn, MacPeak and Seas

[57] ABSTRACT

A silver halide photographic light-sensitive material comprising a support having thereon at least one silver halide emulsion layer, the photographic light-sensitive material containing a color image forming coupler comprising a nitrogen containing heterocyclic 5-membered ring-condensed-5-membered ring in which the coupling active position is substituted with the nitrogen atom of a carboxylic acid amido group containing at least one fluorine atom.

The magenta color image forming coupler has good color forming property and provides a magenta color image having excellent spectral absorption property and good fastness to light.

28 Claims, No Drawings

SILVER HALIDE PHOTOGRAPHIC LIGHT-SENSITIVE MATERIAL

FIELD OF THE INVENTION

The present invention relates to a silver halide photographic light-sensitive material containing a novel color image forming coupler of the nitrogen containing heterocyclic 5-membered ring-condensed-5-membered ring type. More specifically, it relates to a silver halide photographic light-sensitive material containing a magenta color image forming coupler which has a good color forming property and can form color image having excellent color hue and good fastness, particularly good fastness to light.

BACKGROUND OF THE INVENTION

It is well known that when a silver halide color photographic light-sensitive material is subjected to color development, an oxidized aromatic primary amine color developing agent reacts with a coupler to form a dye such as an indophenol, an indoaniline, an indamine, an azomethine, a phenoxazine, a phenazine and the like, thus forming a color image. In order to form a magenta color image, a 5-pyrazolone type coupler, a cyanoacetophenone type coupler, an indazolone type coupler, a pyrazolobenzimidazole type coupler or a pyrazolotriazole type coupler is generally employed.

Magenta color image forming couplers which have been widely used in practice and on which various investigations have been made are almost all 5-pyrazolones. It is known that dyes formed from 5-pyrazolone type couplers are excellent in fastness to heat and light but they have an undesirable absorption of yellow component in the region around 430 nm, which causes color turbidity.

In order to reduce yellow component absorption, a pyrazolobenzimidazole nucleus as described in British Pat. No. 1,047,612, an indazolone nucleus as described in U.S. Pat. No. 3,770,447 and a 1H-pyrazolo[3,2-c][1,2,4]triazole nucleus as described in U.S. Pat. No. 3,725,067 have been proposed as a magenta color image forming coupler skeleton. Further, a 1H-imidazo[1,2-b]pyrazole nucleus as described in Japanese Patent Application No. 23434/83, a 1H-pyrazolo[1,5-b][1,2,4]triazole nucleus as described in Japanese Patent Application No. 45512/83, a 1H-pyrazolo[1,5-d]tetrazole nucleus as described in Japanese Patent Application No. 142801/83 and a 1H-pyrazolo[1,5-b]pyrazole nucleus as described in Japanese Patent Application No. 151354/83 have been recently proposed as novel magenta color image forming coupler skeletons.

The magenta dyes formed from the 1H-pyrazolo-[3,2-c][1,2,4]triazole type couplers as described in U.S. Pat. No. 3,725,067 and British Pat. Nos. 1,252,418 and 1,334,515; the 1H-imidazo[1,2-b]pyrazole type couplers as described in Japanese Patent Application No. 23434/83; the 1H-pyrazolo[1,5-b][1,2,4]triazole type couplers as described in Japanese Patent Application No. 45512/83; the 1H-pyrazolo[1,5-d]tetrazole type couplers as described in Japanese Patent Application No. 142801/83; and the 1H-pyrazolo[1,5-b]pyrazole type couplers as described in Japanese Patent Application No. 151354/83 among these magenta dye image forming couplers show excellent absorption characteristics free from the undesirable absorption of yellow component as described above in a solvent such as ethyl acetate, dibutyl phthalate, etc., and thus they provide preferable color separation.

Of these magenta couplers, however, the 1H-pyrazolo[3,2-c][1,2,4]triazole type couplers have only poor color forming property which results in a decrease in sensitivity and/or a decrease in the maximum color image density obtained Also, azomethine dyes formed from these couplers have remarkably low fastness to light and greatly reduce the desired properties of color photographic light-sensitive materials, in particular, color photographic light-sensitive materials for prints. On the other hand, other novel nitrogen containing heterocyclic 5-membered ring-condensed-5-membered ring type couplers as described above have improved color forming property and provide azomethine dyes having improved light fastness. However, it has been desired in the art to further improve these properties for use in color photographic light-sensitive materials, particularly in color photographic light-sensitive materials for prints.

SUMMARY OF THE INVENTION

An object of the present invention is to provide a silver halide photographic light-sensitive material containing a novel color image forming coupler of the nitrogen containing heterocyclic 5-membered ring-condensed-5-membered ring type having excellent color forming property.

Another object of the present invention is to provide a silver halide photographic light-sensitive material containing a magenta color image forming coupler which has an improved color forming property and provides a color image having an improved color hue and improved fastness.

A further object of the present invention is to provide a silver halide color photographic light-sensitive material which is favorable in color separation and color reproduction and particularly which has a color image of improved fastness to light.

Other objects of the present invention will become apparent from the following detailed description and examples.

These objects of the present invention are achieved by a silver halide photographic light-sensitive material comprising a support having thereon at least one silver halide emulsion layer, the photographic light-sensitive material containing a color image forming coupler comprising a nitrogen containing heterocyclic 5-membered ring-condensed-5-membered ring in which the coupling active position is substituted with the nitrogen atom of a carboxylic acid amido group containing at least one fluorine atom.

DETAILED DESCRIPTION OF THE INVENTION

The color image forming coupler of the nitrogen containing heterocyclic 5-membered ring-condensed-5-membered ring type (hereinafter referred to merely as a "5,5-N-heterocyclic coupler") as effectively used in the present invention is a color image forming coupler which is characterized in its structure by having the skeleton in which a 5-membered ring containing at least one nitrogen atom is condensed at the 1-position and the 5-position of a pyrazole ring and by being substituted at the coupling active position thereof with the nitrogen atom of an N-unsubstituted or N-substituted primary carboxylic acid amido group (including a cyclic structure formed from an N-substituent together with an acyl group, and a cyclic imido group) containing at least one fluorine atom.

Preferred 5,5-N-heterocyclic couplers can be represented by the following general formula (I):

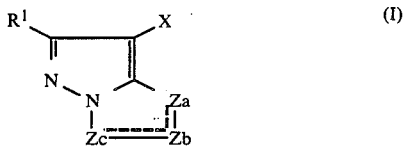

wherein X represents a group capable of being released upon coupling which is represented by general formula (II) described below; $R^1$ represents a hydrogen atom or a substituent (examples of the substituent include a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group and an aryloxycarbonyl group); Za, Zb and Zc each represents a methine group, a substituted methine group, a methylene group, a substituted methylene group, =N— or —NH—, one of the Za—Zb bond and the Zb—Zc bond being a double bond and the other being a single bond; $R^1$ or X may also form a polymer including a dimer or more; and when Za, Zb or Zc is a substituted methine group, the substituted methine group may form a polymer including a dimer or more.

wherein $R^2$ represents an alkyl group substituted with at least one and preferably at most 30 fluorine atoms (preferably an alkyl group containing from 1 to 36 carbon atoms, such as a difluoromethyl group, a trifluoromethyl group, a heptafluoropropyl group, a 1,1,2,2,3,3,4,4-octafluorobutyl group, a pentadecafluoroheptyl group, a 1,1,2,2,3,3,4,4,5,5,6,6,7,7,8,8-hexadecafluorooctyl group, etc., and an alkyl group which may be further substituted with a halogen atom other than a fluorine atom, a hydroxyl group, a cyano group, an aryl group, a heterocyclic group, a carboxyl group, an alkoxy group, an aryloxy group, an acylamino group, a sulfonamido group, an imido group, an alkoxycarbonyl group, an aryloxycarbonyl group, an alkylthio group, an arylthio group, an alkylsulfonyl group, an arylsulfonyl group, a carbamoyl group, a sulfamoyl group, an alkoxycarbonylamino group, an aryloxycarbonylamino group, a ureido group, an acyl group, an alkylamino group or an arylamino group), an aryl group substituted with at least one and preferably at most 30 fluorine atoms (preferably an aryl group containing from 6 to 32 carbon atoms, such as a 2-fluorophenyl group, a 2,6-difluorophenyl group, a pentafluorophenyl group, etc., and an aryl group which may be further substituted with a substituent selected from those as defined for the foregoing alkyl group represented by $R^2$ or the like), or a heterocyclic group substituted with at least one and preferably at most 30 fluorine atoms (which may be further substituted with a substituent selected from those as defined for the foregoing alkyl group represented by $R^2$);

$R^3$ represents a hydrogen atom, an alkyl group (preferably an alkyl group containing from 1 to 22 carbon atoms, such as a methyl group, an ethyl group, a butyl group, an octyl group, a 2-ethylhexyl group, and an alkyl group substituted with a halogen atom, a hydroxyl group, a cyano group, an aryl group, a carboxyl group, an alkoxyl group, an aryloxy group, an acylamino group, a sulfonamido group, an imido group, an alkoxycarbonyl group, an aryloxycarbonyl group, an alkylthio group, an arylthio group, an alkylsulfonyl group, an arylsulfonyl group, a carbamoyl group, a sulfamoyl group, an alkyloxycarbonylamino group, an aryloxycarbonylamino group, a ureido group, an acyl group, an alkylamino group or an arylamino group), an aryl group (preferably an aryl group containing from 6 to 32 carbon atoms, such as a phenyl group, a naphthyl group, and an aryl group which may be substituted with a substituent selected from those as defined for the foregoing alkyl group represented by $R^3$), a heterocyclic group (e.g., a 2-pyridyl group, a 2-quinolyl group, a 2-benzothiazolyl group, a 2-furyl group or a 2-pyrimidinyl group, etc.), an acyl group (e.g., an acetyl group, a butanoyl group, a hexanoyl group, a trifluoroacetyl group, a heptafluorobutanoyl group, a benzoyl group, a naphthoyl group, a pentafluorobenzoyl group, a pentachlorophenyl group, a 2-furancarbonyl group or a 2-quinolinecarbonyl group, etc.), a sulfonyl group (e.g., a methanesulfonyl group, a hexanesulfonyl group, a benzenesulfonyl group, a naphthalenesulfonyl group, and an alkylsulfonyl group or arylsulfonyl group which may be substituted with a substituent selected from those as defined for the foregoing alkyl group represented by $R^3$, etc.), a carbamoyl group (e.g., an N-methylcarbamoyl group, an N-dodecylcarbamoyl group, an N,N-diethylcarbamoyl group, an N-phenylcarbamoyl group, and an N-alkylcarbamoyl group, N,N-dialkylcarbamoyl group, N-arylcarbamoyl group, or N,N-diarylcarbamoyl group which may be substituted with a substituent selected from those as defined for the foregoing alkyl group represented by $R^3$, etc.), a sulfamoyl group (e.g., an N-methylsulfamoyl group, an N-n-octylsulfamoyl group, an N-phenylsulfamoyl group, an N,N-diethylsulfamoyl group, and an N-alkylsulfamoyl group, N,N-dialkylsulfamoyl group, N-arylsulfamoyl group, or N,N-diarylsulfamoyl group which may be substituted with a substituent selected from those as defined for the foregoing alkyl group represented by $R^3$, etc.), an alkoxycarbonyl group (e.g., a methoxycarbonyl group, a butyloxycarbonyl group, a dodecyloxycarbonyl group, a 2-ethylhexyloxycarbonyl group, and an alkoxycarbonyl group which may be substituted with a substituent selected from those as defined for the foregoing alkyl group represented by $R^3$, etc.), or an aryloxycarbonyl group (e.g., a phenoxycarbonyl group, a 1-naphthoxycarbonyl group, and an aryloxycarbonyl group which may be substituted with a substituent selected from those as defined for the foregoing alkyl group represented by $R^3$, etc.); or $R^2$ and $R^3$ may also combine together with the nitrogen atom to form a 5-membered or 6-membered ring, which may be further condensed to a benzene ring or a heterocyclic ring.

The 5-membered or 6-membered ring formed by $R^2$ and $R^3$ together with the nitrogen atom includes a cyclic imido group having at least one fluorine atom on the ring or in a substituent attached to the ring (e.g., a 3,4-difluoro-N-succinimido group, a tetrafluoro-N-phthalimido group, etc., and the foregoing cyclic imido group which is further substituted with a halogen atom other than a fluorine atom, a cyano group, a nitro group, an alkyl group, an aryl group, a carboxyl group, an alkoxyl group, an aryloxy group, an acylamino group, a sulfonamido group, a hydroxyl group, an imido group, an alkoxycarbonyl group, an aryloxycarbonyl group, an alkylthio group, an arylthio group, an alkylsulfonyl group, an arylsulfonyl group, a carbamoyl group, a sulfamoyl group, an alkoxycarbonylamino group, an aryloxycarbonylamino group, a ureido group, an acyl group, an alkylamino group or an arylamino group), a 2-N-1,1-dioxo-3-(2H)-oxo-1,2-benzisothiazolyl group (saccharin) having at least one fluorine atom on the ring or in a substituent attached to the ring, a 2-N-1,1-dioxo-3-(2H)-oxo-1,2-benzisothiazolyl group which may be further substituted with a substituent selected from those as defined for the foregoing cyclic imido group, a group having at least one fluorine atom on the ring or in a substituent attached to the ring and being represented by the formula:

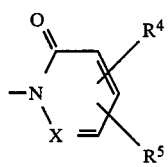

wherein X represents —CH= or —N=; and $R^4$ and $R^5$ each represents a hydrogen atom, a fluorine atom or a substituent selected from those as defined for the foregoing cyclic imido group or $R^4$ and $R^5$ combine together to form a condensed ring, or a group having at least one fluorine atom on the ring or in a substituent attached to the ring and being represented by the formula:

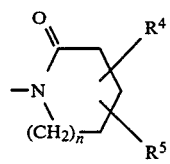

wherein n represents 1 or 2; and $R^4$ and $R^5$ each represents a hydrogen atom, a fluorine atom or a substituent selected from those as defined for the foregoing cyclic imido group or $R^4$ and $R^5$ may combine together to form a condensed ring (e.g., a 3-fluoro-2-oxo-1-pyrrolidinyl group, etc.).

The 5,5-N-heterocyclic coupler represented by general formula (I) provides a dye having less subsidiary absorption of yellow component and good color separation at a favorable color forming rate in comparison with 5-pyrazolone type couplers hitherto publicly used.

Among the 5,5-N-heterocyclic couplers represented by general formula (I), those of general formula (I) in which Za, Zb and Zc each represents an unsubstituted or substituted methine group are more preferred. Such 5,5-N-heterocyclic couplers provide a dye which has the absorption property that its main absorption maximum is present in the wavelength range of 500 nm to 580 nm, that undesirable yellow absorption is remarkably less and that the absorption at the long wavelength side is sharply cut, is fast to light and forms at a good color forming rate upon coupling reaction with the oxidation product of an aromatic primary amine developing agent.

Particularly preferred 5,5-N-heterocyclic couplers which can be used in the present invention are those represented by the following general formula (III), (IV), (V), (VI) or (VII):

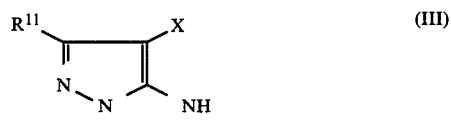

(III)

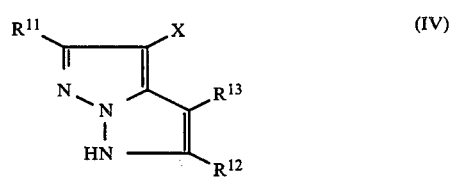

(IV)

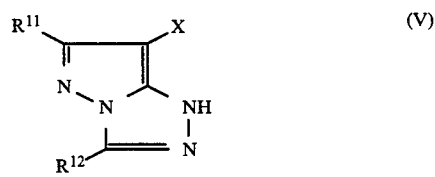

(V)

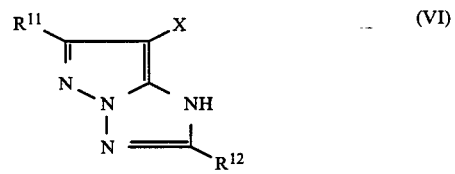

(VI)

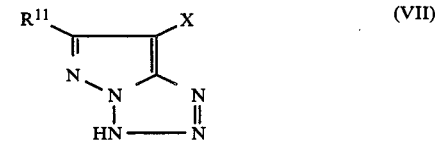

(VII)

In general formula (III), (IV), (V), (VI) or (VII), preferably $R^{11}$, $R^{12}$ and $R^{13}$ each represents a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group or an aryloxycarbonyl group; and X represents a hydrogen atom, a halogen atom, a carboxyl group or a group capable of being released upon coupling which is bonded to the carbon atom at the coupling position through an oxygen atom, a nitrogen atom or a sulfur atom. Also, $R^{11}$, $R^{12}$, $R^{13}$ or X may be a divalent group to form a bis coupler. Further, the coupler shown by general formula (III), (IV), (V), (VI) or (VII) may be in the form of a polymer coupler having a molecular weight of preferably about 2,000 to 200,000 in which the coupler moiety exists at the main chain or the side chain of the polymer and particularly a polymer coupler derived from a vinyl monomer having the coupler moiety shown by general formulae (III) to (VII) described above is preferred. In this case, $R^{11}$, $R^{12}$, $R^{13}$ or X represents a vinyl group or a linking group.

In more detail, $R^{11}$, $R^{12}$ and $R^{13}$ each represents a hydrogen atom, a halogen atom (e.g., a chlorine atom, a bromine atom, etc.), an alkyl group (e.g., a methyl group, a propyl group, a tert-butyl group, a trifluoromethyl group, a tridecyl group, a 3-(2,4-di-tert-amylphenoxy)propyl group, an allyl group, a 2-dodecyloxyethyl group, a 3-phenoxypropyl group, a 2-hexylsulfonylethyl group, a cyclopentyl group, a benzyl group, etc.), an aryl group (e.g., a phenyl group, a 4-tert-butylphenyl group, a 2,4-di-tert-amylphenyl group, a 4-tetradecanamidophenyl group, etc.), a heterocyclic group (e.g., a 2-furyl group, a 2-thienyl group, a 2-pyrimidinyl group, a 2-benzothiazolyl group, etc.), a cyano group, an alkoxy group (e.g., a methoxy group, an ethoxy group, a 2-methoxyethoxy group, a 2-dodecyloxyethoxy group, a 2-methanesulfonylethoxy group, etc.), an aryloxy group (e.g., a phenoxy group, a 2-methylphenoxy group, a 4-tert-butylphenoxy group, etc.), a heterocyclic oxy group (e.g., a 2-benzimidazolyloxy group, etc.), an acyloxy group (e.g., an acetoxy group, a hexadecanoyloxy group, etc.), a carbamoyloxy group (e.g., an N-phenylcarbamoyloxy group, an N-ethylcarbamoyloxy group, etc.), a silyloxy group (e.g., a trimethylsilyloxy group, etc.), a sulfonyloxy group (e.g., a dodecylsulfonyloxy group, etc.), an acylamino group (e.g., an acetamido group, a benzamido group, a tetradecanamido group, an α-(2,4-di-tert-amylphenoxy)-butylamido group, a γ-(3-tert-butyl-4-hydroxyphenoxy)-butylamido group, an α-[4-(4-hydroxyphenylsulfonyl)-phenoxy]decanamido group, etc.), an anilino group (e.g., a phenylamino group, a 2-chloroanilino group, a 2-chloro-5-tetradecanamidoanilino group, a 2-chloro-5-dodecyloxycarbonylanilino group, an N-acetylanilino group, a 2-chloro-5-[α-(3-tert-butyl-4-hydroxyphenoxy)dodecanamido]-anilino group, etc.), a ureido group (e.g., a phenylureido group, a methylureido group, an N,N-dibutylureido group, etc.), an imido group (e.g., an N-succinimido group, a 3-benzylhydantoinyl group, a 4-(2-ethylhexanoylamino)phthalimido group, etc.), a sulfamoylamino group (e.g., an N,N-dipropylsulfamoylamino group, an N-methyl-N-decylsulfamoylamino group, etc.), an alkylthio group (e.g., a methylthio group, an octylthio group, a tetradecylthio group, a 2-phenoxyethylthio group, a 3-phenoxypropylthio group, a 3-(4-tert-butylphenoxy)propylthio group, etc.), an arylthio group (e.g., a phenylthio group, a 2-butoxy-5-tert-octylphenylthio group, a 3-pentadecylphenylthio group, a 2-carboxyphenylthio group, a 4-tetradecanamidophenylthio group, etc.), a heterocyclic thio group (e.g., a 2-benzothiazolylthio group, etc.), an alkoxycarbonylamino group (e.g., a methoxycarbonylamino group, a tetradecyloxycarbonylamino group, etc.), an aryloxycarbonylamino group (e.g., a phenoxycarbonylamino group, a 2,4-di-tert-butylphenoxycarbonylamino group, etc.), a sulfonamido group (e.g., a methanesulfonamido group, a hexadecanesulfonamido group, a benzenesulfonamido group, a p-toluenesulfonamido group, an octadecanesulfonamido group, a 2-methyloxy-5-t-butylbenzenesulfonamido group, etc.), a carbamoyl group (e.g., an N-ethylcarbamoyl group, an N,N-dibutylcarbamoyl group, an N-(2-dodecyloxyethyl)carbamoyl group, an N-methyl-N-dodecylcarbamoyl group, an N-[3-(2,4-di-tert-amylphenoxy)propyl]carbamoyl group, etc.), an acyl group (e.g., an acetyl group, a (2,4-di-tert-amylphenoxy)acetyl group, a benzoyl group, etc.), a sulfamoyl group (e.g., an N-ethylsulfamoyl group, an N,N-dipropylsulfamoyl group, an N-(2-dodecyloxyethyl)sulfamoyl group, an N-ethyl-N-dodecylsulfamoyl group, an N,N-diethylsulfamoyl group, etc.), a sulfonyl group (e.g., a methanesulfonyl group, an octanesulfonyl group, a benzenesulfonyl group, a toluenesulfonyl group, etc.), a sulfinyl group (e.g., an octanesulfinyl group, a dodecylsulfinyl group, a phenylsulfinyl group, etc.), an alkoxycarbonyl group (e.g., a methoxycarbonyl group, a butyloxycarbonyl group, a dodecylcarbonyl group, an octadecylcarbonyl group, etc.) or an aryloxycarbonyl group (e.g., a phenyloxycarbonyl group, a 3-pentadecyloxycarbonyl group, etc.).

In the coupler represented by general formula (III), $R^{12}$ and $R^{13}$ may combine with each other to form a 5-membered, 6-membered or 7-membered nonaromatic ring.

In the coupler represented by general formula (IV), $R^{12}$ and $R^{13}$ may combine with each other to form a 5-membered, 6-membered or 7-membered saturated, unsaturated or aromatic ring.

Examples of the group capable of being released, upon coupling represented by X include a group represented by general formula (II) described above.

When $R^{11}$, $R^{12}$, $R^{13}$ or X represents a divalent group to form a bis coupler, $R^{11}$, $R^{12}$ or $R^{13}$ preferably represents a substituted or unsubstituted alkylene group (e.g., a methylene group, an ethylene group, a 1,10-decylene group, $-CH_2CH_2-O-CH_2CH_2-$, etc.), a substituted or unsubstituted phenylene group (e.g., a 1,4-phenylene group, a 1,3-phenylene group,

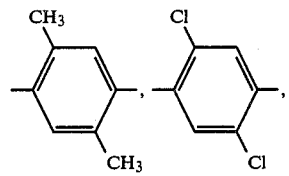

etc.), an $-NHCO-R^{14}-CONH-$ group (wherein $R^{14}$ represents a substituted or unsubstituted alkylene or phenylene group, e.g., $-NHCOCH_2CH_2CONH-$,

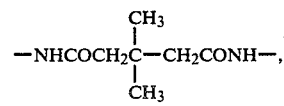

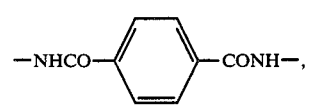

etc.) or an $-S-R^{14}-S-$group (wherein $R^{14}$ represents a substituted or unsubstituted alkylene group e.g., $-S-CH_2CH_2-S-$

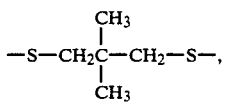

etc.); and X represents a divalent group appropriately formed from the monovalent group for X described above (for example, in general formula (II) for X, $R^2$ or $R^3$ represents an unsubstituted or substituted alkylene group or phenylene group).

The linking group represented by $R^{11}$, $R^{12}$, $R^{13}$ or X in the cases wherein the coupler moiety represented by general formula (III), (IV), (V), (VI) or (VII) is included in a vinyl monomer includes an alkylene group (including a substituted or unsubstituted alkylene group, e.g., a methylene group, an ethylene group, a 1,10-decylene group —CH$_2$CH$_2$OCH$_2$CH$_2$—, etc.), a phenylene group (including a substituted or unsubstituted phenylene group, e.g., a 1,4-phenylene group, a 1,3-phenylene group,

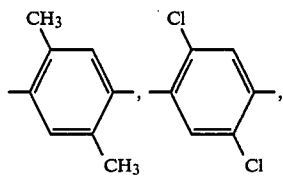

etc.), —NHCO—, —CONH—, —O—, —OCO—, and an aralkylene group (e.g.,

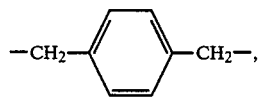

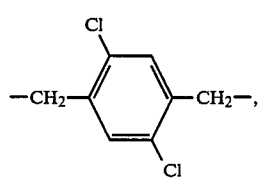

etc.) or a combination thereof.

Specific examples of preferred linking groups are set forth below.

—NHCO—, —CH$_2$CH$_2$—,

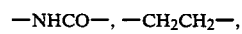

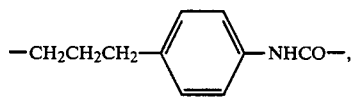

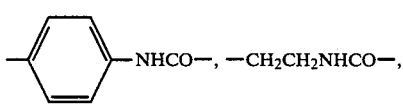

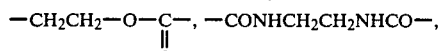

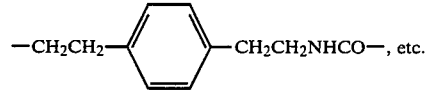

Further, a vinyl group in the vinyl monomer may further have a substituent in addition to the coupler moiety represented by general formula (III), (IV), (V), (VI) or (VII). Preferred examples of the substituents include a hydrogen atom, a chlorine atom or a lower alkyl group having from 1 to 4 carbon atoms (e.g., a methyl group, an ethyl group, etc.).

Among the couplers represented by general formula (III), (IV), (V), (VI) or (VII), the couplers represented by general formula (III), (IV), (VI) or (VII) are preferred in view of the fastness of the dyes formed from the couplers. The couplers represented by general formula (III) or (VI) are particularly preferred in view of the above described point.

A monomer containing the coupler moiety represented by general formula (III), (IV), (V), (VI) or (VII) may form a copolymer together with a non-color forming ethylenic monomer which does not undergo coupling with the oxidation product of a primary aromatic amine developing agent.

Examples of non-color forming ethylenic monomers which do not undergo coupling with the oxidation product of a primary aromatic amine developing agent include acrylic acid and derivatives thereof such as acrylic acid, α-chloroacrylic acid, α-alacrylic acid (e.g., methacrylic acid, etc.), etc., an ester or an amide derived from these acrylic acids (e.g., acrylamide, n-butylacrylamide, tert-butylacrylamide, diacetoneacrylamide, methacrylamide, methyl acrylate, ethyl acrylate, n-propyl acrylate, n-butyl acrylate, tert-butyl acrylate, isobutyl acrylate, 2-ethylhexyl acrylate, n-octyl acrylate, lauryl acrylate, methyl methacrylate, ethyl methacrylate, n-butyl methacrylate, β-hydroxy methacrylate, etc.), methylenedibisacrylamide, a vinyl ester (e.g., vinyl acetate, vinyl propionate, vinyl laurate, etc.), acrylonitrile, methacrylonitrile, an aromatic vinyl compound (e.g., styrene and derivatives thereof, vinyltoluene, divinylbenzene, vinylacetophenone, sulfostyrene, etc.), itaconic acid, citraconic acid, crotonic acid, vinylidene chloride, a vinyl alkyl ether having an alkyl moiety containing 1 to 18 carbon atoms (e.g., vinyl ethyl ether, etc.), maleic acid, maleic anhydride, a maleic acid ester, N-vinyl-2-pyrrolidone, N-vinylpyridine, 2- or 4-vinylpyridine, etc.

Two or more non-color forming ethylenically unsaturated monomers can be used together. For example, a combination of n-butyl acrylate and methyl acrylate, styrene and methacrylic acid, methacrylic acid and acrylamide, methyl acrylate and diacetoneacrylamide, etc., can be used.

As is well known in the field of polymer color couplers, the non-color forming ethylenically unsaturated monomer which is copolymerized with a water-insoluble monomer coupler having a solid or liquid form at ordinary temperature can be selected in such a manner that the copolymer formed has good physical properties and/or chemical properties, for example, solubility, compatibility with a binder in a photographic colloid composition, such as gelatin, flexibility, heat stability, etc.

The polymer couplers used in the present invention may be water-soluble coupler or water-insoluble couplers, but polymer coupler latexes are particularly preferred as such polymer couplers.

Specific examples of representative magenta couplers and monomers for preparing polymer couplers according to the present invention are set forth below, but the present invention should not be construed as being limited thereto.

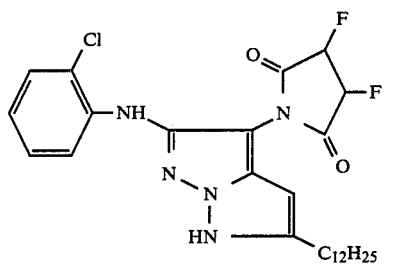

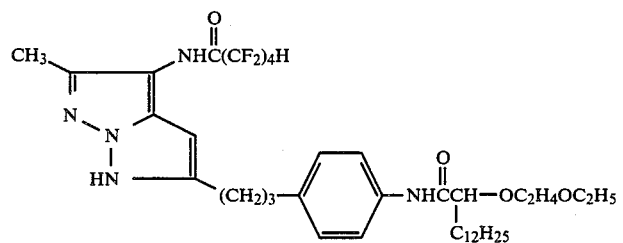

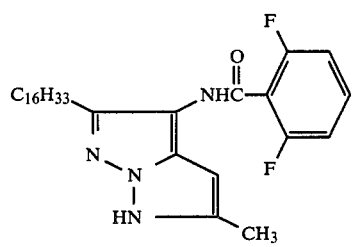

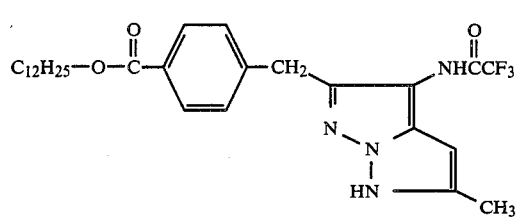

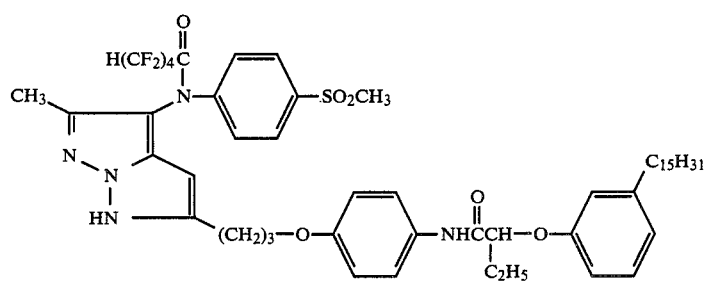

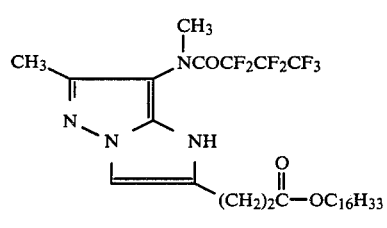

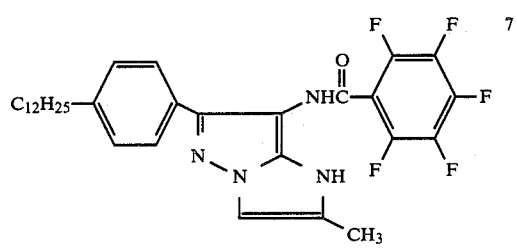

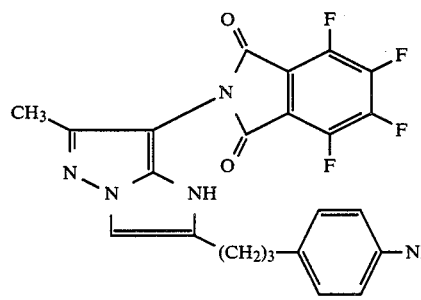

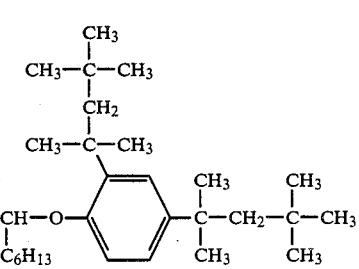

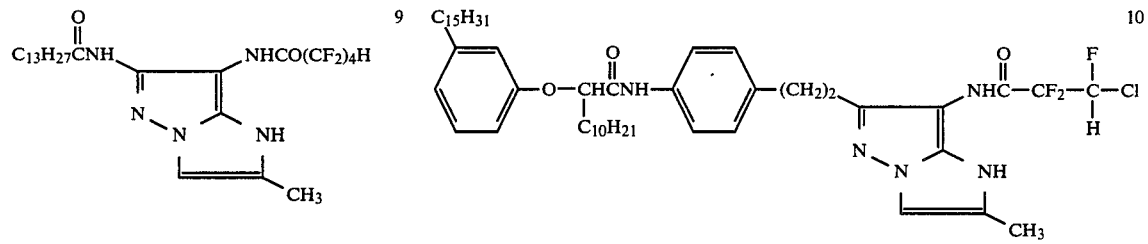
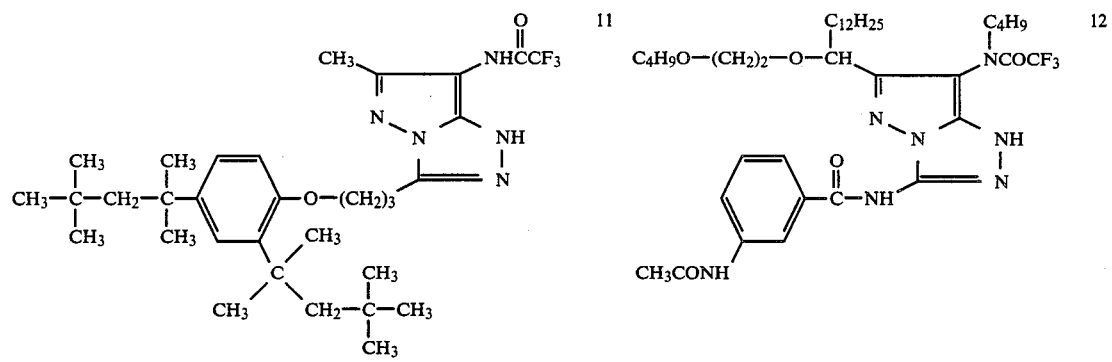
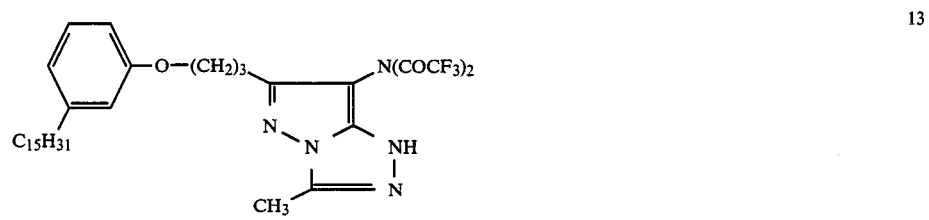
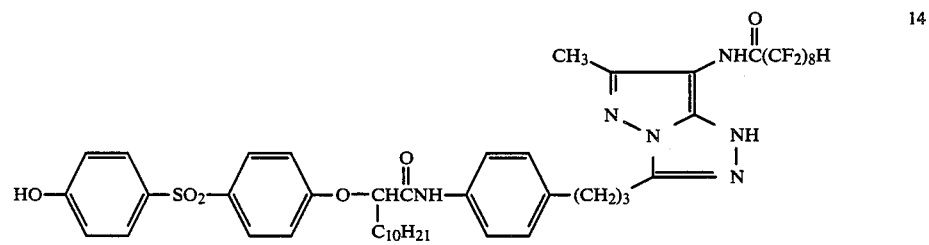
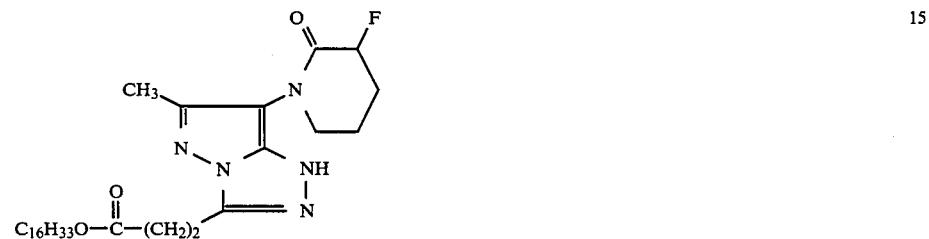
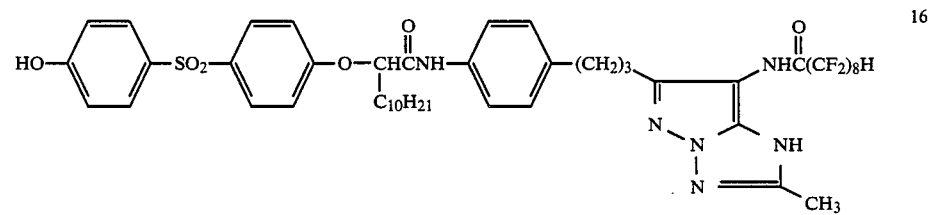

17
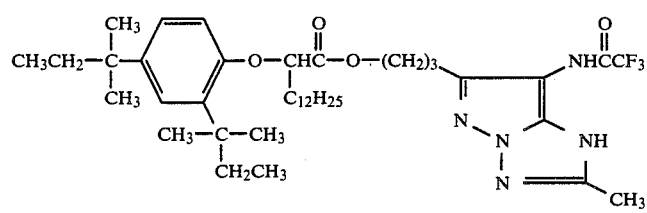
18
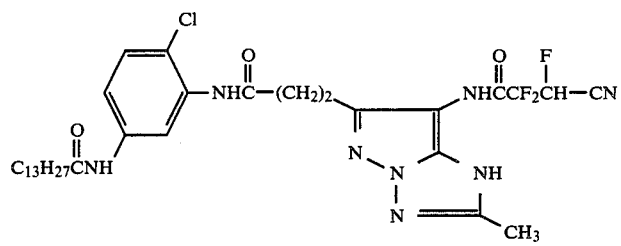
19
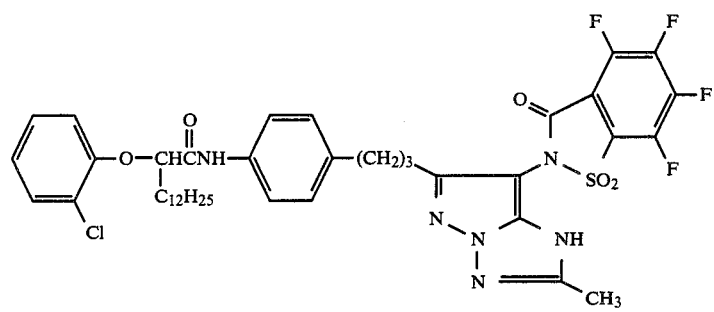
20
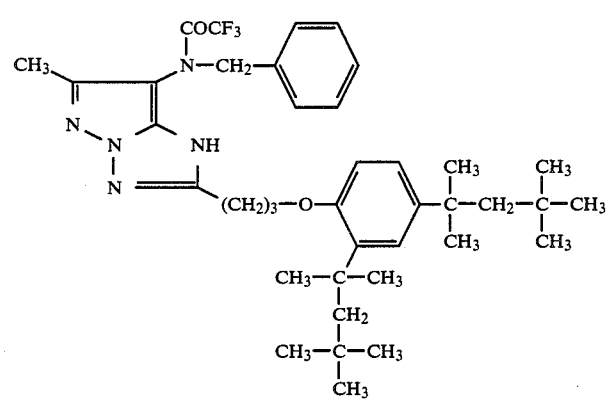
21
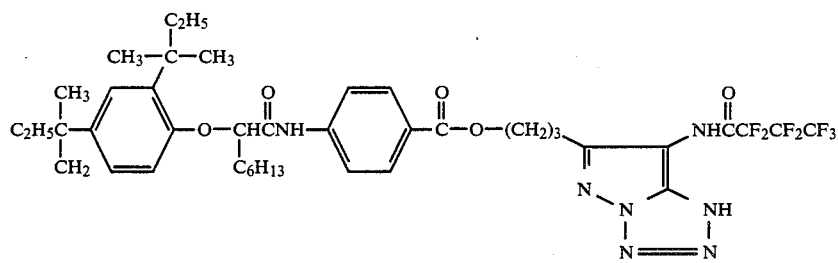
22
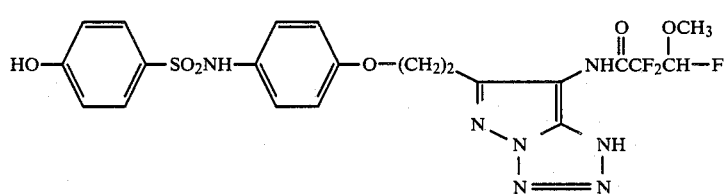

23

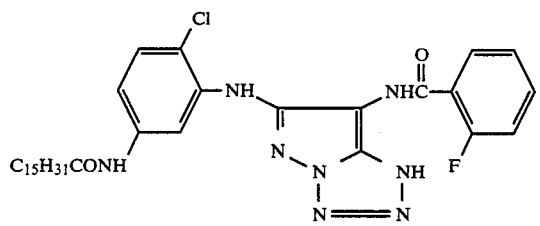

24

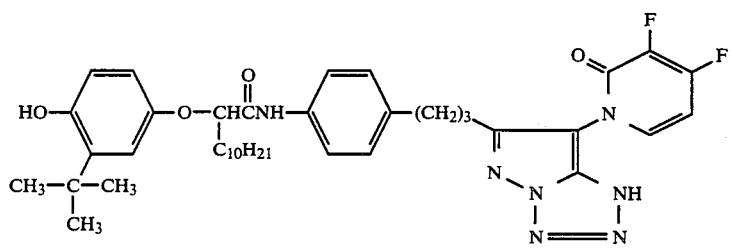

25

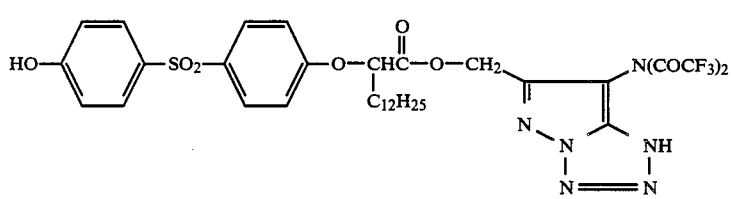

29

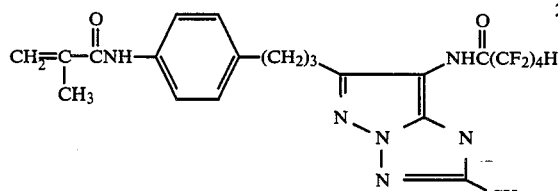

30

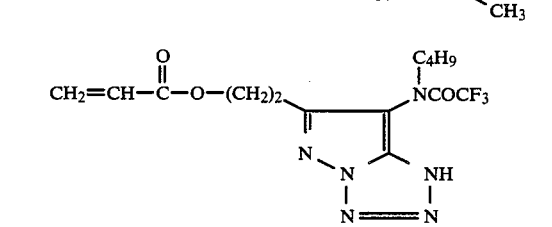

The following are examples of monomers for preparing polymer couplers.

26

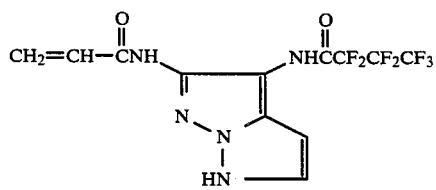

27

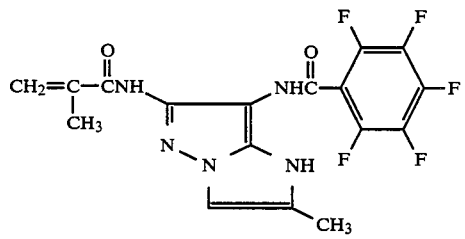

28

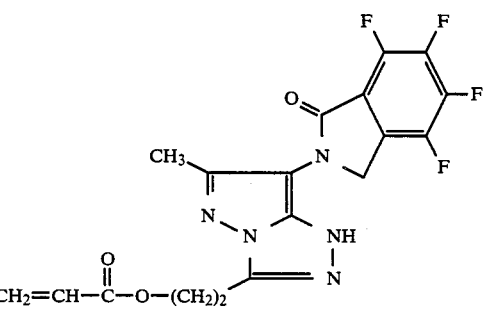

Specific examples of synthesizing the magenta couplers according to the present invention are set forth below.

SYNTHESIS EXAMPLE 1

Synthesis of 3-{3-[2-(2,4-di-tert-amylphenoxy)tetra-decanoyloxy]-propyl}-2-methyl-7-trifluoroacetamido-1H-pyrazolo[1,5-b][1,2,4]triazole [Coupler 17]

15.0 g of 3-{3-[2-(2,4-di-tert-amylphenoxy)-tetradecanoyloxy]propyl}-2-methyl-1H-pyrazolo-[1,5-b][1,2,4]triazole was added to 100 ml of glacial acetic acid and the mixture was stirred at room temperature. To the mixture was added dropwise 10 ml of a glacial acetic acid solution containing 2.81 g of isoamyl nitrite over a period of 10 minutes and the mixture was further stirred for 1 hour. The reaction mixture was poured into 1.6 liters of water with stirring and the precipitate thus formed was collected by filtration, washed with 1 liter of water and dried with calcium chloride in a vacuum desiccator to obtain 15.3 g (yield: 98 mol %) of the 7-nitroso intermediate as milk white powder.

15.3 g of the 7-nitroso intermediate thus obtained was dissolved in 190 ml of ethanol and refluxed by heating with stirring under a nitrogen atmosphere. 45 ml of a concentrated hydrochloric acid solution (12N) containing 22.3 g of stannous chloride was added dropwise to the refluxing solution over a period of 10 minutes. After the completion of the dropwise addition, the reaction mixture was cooled to room temperature, poured into 600 ml of water and extracted with ethyl acetate. The extract was dried with anhydrous magnesium sulfate and concentrated to the dry state. Thus, 21 g of the crude 7-amino intermediate was obtained as a reddish brown powder.

21 g of the crude 7-amino intermediate thus obtained was added to 130 ml of pyridine and stirred under a nitrogen atmosphere with cooling by an ice bath. 12.3 g of anhydrous trifluoroacetic acid was added dropwise to the solution and the mixture was further stirred for 10 minutes. The reaction mixture was poured into 0.8 liter of water and extracted with ethyl acetate. The organic layer was washed with 2N hydrochloric acid and then an aqueous saturated sodium chloride solution, dried with anhydrous magnesium sulfate and concentrated. The residue was separated using silica gel column chromatography (silica gel: 400 g; solvent: chloroform and methanol=70:1 by volume) and the eluate was concentrated to the dry state to obtain 11.7 g (yield: 68 mol % based on the 7-nitroso intermediate) of Coupler 17 as a white powder. Elemental Analysis:

|  | H | C | N |
|---|---|---|---|
| Calculated (%): | 8.51 | 65.46 | 9.54 |
| Found (%): | 8.66 | 65.27 | 9.47 |

SYNTHESIS EXAMPLE 2

Synthesis of 3-[3-(4-{2-[4-(4-benzyloxyphenylsulfonyl)-phenoxy]-dodecanamido}phenyl)propyl]-7-hexadecafluorononanamido-6-methyl-1H-pyrazolo[3,2-c][1,2,4]triazole [Coupler 14]

38.8 g of 6-methyl-3-[3-(4-{2-[4-(4-benzyloxyphenylsulfonyl)phenoxy]dodecanamido}phenyl)propyl]-1H-pyrazolo[3,2-c][1,2,4]triazole was added to 200 ml of glacial acetic acid and suspended therein with stirring. To the suspension was added dropwise 40 ml of a glacial acetic acid solution containing 5.86 g of isoamyl nitrite at room temperature over a period of 10 minutes followed by stirring for 1.5 hours. The reaction mixture was poured into 3 liters of water and thoroughly stirred. The precipitate thus formed was collected by filtration, washed with 5 liters of water and dried with calcium chloride in a vacuum desiccator to obtain 39.0 g (yield: 97 mol %) of the 7-nitroso intermediate as a milk white powder.

7.2 g of the 7-nitroso intermediate thus obtained was dissolved in 80 ml of ethanol and refluxed by heating with stirring under a nitrogen atmosphere. 15 ml of a concentrated hydrochloric acid solution (12N) containing 8.5 g of stannous chloride was added dropwise to the solution. After the completion of the dropwise addition, the reaction mixture was cooled to room temperature, poured into 250 ml of water and extracted with ethyl acetate. The organic layer was dried with anhydrous magnesium sulfate and concentrated to the dry state. Thus, 10 g of the crude 7-amino intermediate was obtained as dark orange powder.

10 g of the crude 7-amino intermediate thus obtained was added to 50 ml of pyridine and stirred under a nitrogen atmosphere with cooling by a water bath. 5.38 g of hexadecafluorononanoyl chloride was added dropwise to the mixture and the mixture was further stirred for 1 hour. The reaction mixture was poured into 500 ml of water and extracted with ethyl acetate. The organic layer was washed with water, dried with anhydrous magnesium sulfate and concentrated. The residue was separated using silica gel column chromatography (silica gel: 300 g; solvent: chloroform and methanol=100:1 by volume) and the eluate was concentrated to the dry state to obtain 7.1 g (yield: 65 mol % based on the 7-nitroso intermediate) of the benzyl derivative of Coupler 14. The benzyl derivative thus obtained was dissolved in 60 ml of tetrahydrofuran and stirred for 16 hours at 60° C. under 50 hydrogen atmospheres in the presence of 1.0 g of 10% palladium-carbon. The catalyst was removed by filtration and the filtrate was concentrated and separated using silica gel column chromatography (silica gel: 100 g; solvent: chloroform and methanol=50:1 by volume). The eluate was concentrated to the dry state to obtain 5.3 g (yield: 81 mol %) of Coupler 14 as a white powder. Elemental Analysis:

|  | H | C | N |
|---|---|---|---|
| Calculated (%): | 4.29 | 50.00 | 7.44 |
| Found (%): | 4.32 | 49.79 | 7.41 |

The amount of couplers of the present invention can be varied depending on the type of the couplers but a range of from about 0.002 to 0.5 mol, preferably about 0.005 to 0.1 mol, per mol of silver halide is used. When the couplers are polymer couplers, the above amounts correspond to the mol of coupler moieties in the polymer couplers.

The photographic emulsion layers of the photographic light-sensitive materials of the present invention can contain, in addition to the couplers according to the present invention, other conventional color image forming couplers, i.e., compounds capable of forming color upon oxidative coupling with aromatic primary amine developing agents (e.g., phenylenediamine derivatives, aminophenol derivatives, etc.) during the course of color development processing. Examples of such couplers include magenta couplers, such as 5-pyrazolone couplers, pyrazolobenzimidazole couplers, cyanoacetylcoumarone couplers and open chain acylacetonitrile couplers, etc.; yellow couplers, such as acylacetamide couplers (e.g., benzoylacetanilides, pivaloylacetanilides, etc.), etc.; and cyan couplers, such as naphthol couplers and phenol couplers, etc. It is preferred to use non-diffusible couplers containing a hydrophobic group (a ballast group) within the molecule or polymeric couplers. They may be either 4-equivalent or 2-equivalent with respect to silver ions. It is also possible to use colored couplers capable of exerting color correction effects, or couplers capable of releasing development inhibitors during the course of development (DIR couplers).

Further, the emulsion layers may contain non-color forming DIR coupling compounds which release a development inhibitor, the product of which formed by a coupling reaction is colorless, other than DIR couplers.

Moreover, the photographic light-sensitive materials may contain compounds which release a development inhibitor during the course of development other than DIR couplers.

Two or more kinds of the above described couplers and the like can be present together in the same layer for the purpose of satisfying the properties required of the photographic light-sensitive materials, or the same compound can be added to two or more layers.

It is advantageous to select photographic color couplers to be used for natural color photography so as to provide images of neutral gray. It is preferred that cyan dyes formed from cyan color forming couplers exhibit their maximum absorption bands in the wavelength range from about 600 nm to 720 nm, magenta dyes formed from magenta color forming couplers exhibit their maximum absorption bands in the wavelength range from about 500 nm to 580 nm, and yellow dyes formed from yellow color forming couplers exhibit their maximum absorption bands in the wavelength range from about 400 nm to 480 nm.

The present invention can be applied to conventional silver halide color photographic light-sensitive materials, for example, color negative films, color paper, color positive films, color reversal films for slides, color reversal films for the cinema, color reversal films for TV, etc. In particular, excellent effects in improving color reproducibility, increasing sensitivity and the fastness of color images are achieved when the present invention is utilized in color paper, color negative films and various color reversal films requiring color images of good fastness and high quality.

The present invention can also be applied to black-and-white photographic light-sensitive materials, particularly to black-and-white photographic light-sensitive materials employing a three color coupler mixing process. The three color coupler mixing process is described in detail in *Research Disclosure*, No. 1712, etc. This process is utilizable, for example, in X-ray films to obtain favorable black-and-gray images.

The present invention is also applicable to multilayer multicolor photographic materials having at least two layers sensitive to different spectral wavelength ranges on a support. The multilayer natural color photographic materials generally have at least one red-sensitive emulsion layer, at least one green-sensitive emulsion layer and at least one blue-sensitive emulsion layer on a support. The order of superposition of these layers can be suitably varied. It is ordinarily the case that the red-sensitive emulsion layer contains a cyan forming coupler, the green-sensitive emulsion layer contains a magenta forming coupler and the blue-sensitive emulsion layer contains a yellow forming coupler, respectively. However, if desired or necessary, other combinations may be utilized.

The present invention particularly advantageously increases sensitivity when it is applied to photographic light-sensitive materials having at least two emulsion layers which are sensitive to the same spectral wavelength range but which have different sensitivities from each other. The reason for this is explained in British Pat. No. 923,045. Further, photographic light-sensitive materials of high sensitivity and good color separation can be obtained by using the couplers according to the present invention in photographic light-sensitive materials having at least three emulsion layers which are sensitive to the same spectral wavelength range but have different sensitivities from each other.

In order to incorporate couplers into silver halide emulsion layers, known methods, including those described, for example, in U.S. Pat. No. 2,322,027, etc., may be used. For example, the couplers can be dissolved in a solvent and then dispersed in a hydrophilic colloid. Examples of solvents usable for this process include organic solvents having a high boiling point, such as alkyl esters of phthalic acid (e.g., dibutyl phthalate, dioctyl phthalate, etc ), phosphates (e.g., diphenyl phosphate, triphenyl phosphate, tricresyl phosphate, dioctyl butyl phosphate, etc.), citrates (e.g., tributyl acetyl citrate, etc.), benzoates (e.g., octyl benzoate, etc.), alkylamides (e.g., diethyl laurylamides, etc.), esters of fatty acids (e.g., dibutoxyethyl succinate, dioctyl azelate,, etc.) and trimesates (e.g., tributyl trimesate, etc.); and organic solvents having a low boiling point of from about 30° to about 150° C., such as lower alkyl acetates (e.g., ethyl acetate, butyl acetate, etc.), ethyl propionate, secondary butyl alcohol, methyl isobutyl ketone, $\beta$-ethoxyethyl acetate, methyl Cellosolve acetate, or the like. Mixtures of organic solvents having a high boiling point and organic solvents having a low boiling point can also be used.

It is also possible to utilize the dispersing method using polymers, as described in Japanese Patent Publication No. 39853/76 and Japanese Patent Application (OPI) No. 59943/76 (the term "OPI" as used herein refers to a "published unexamined Japanese patent application").

Of the couplers, those having an acid group, such as a carboxylic acid group or a sulfonic acid group, can be introduced into hydrophilic colloids as an aqueous alkaline solution.

As a binder or a protective colloid for the photographic emulsion, gelatin is advantageously used, but other hydrophilic colloids can be used.

For example, it is possible to use proteins such as gelatin derivatives, graft polymers of gelatin and other high molecular substances, albumin, casein, etc.; saccharides such as cellulose derivatives such as hydroxyethyl cellulose, carboxymethyl cellulose, cellulose sulfate, etc., sodium alginate, starch derivatives, etc.; and various synthetic hydrophilic high molecular weight substances such as homopolymers or copolymers, for example, polyvinyl alcohol, polyvinyl alcohol semiacetal, poly-N-vinylpyrrolidone, polyacrylic acid, polymethacrylic acid, polyacrylamide, polyvinylimidazole, polyvinylpyrazole, etc.

In the photographic emulsion layers of the photographic light-sensitive material used in the present invention, any of silver bromide, silver iodobromide, silver iodochlorobromide, silver chlorobromide and silver chloride may be used as the silver halide. A preferred silver halide is silver iodobromide containing 15 mol % or less of silver iodide, and a particularly preferred silver halide is silver iodobromide containing from 2 mol % to 12 mol % silver iodide.

Although the mean grain size of silver halide particles in the photographic emulsion (the mean grain size being determined with grain diameter in those particles which are spherical or nearly spherical and edge length in those particles which are cubic, and is expressed as a mean value calculated from projected areas) is not particularly limited, but is is preferably 3$\mu$ or less.

The grain size distribution may be broad or narrow.

Silver halide particles in the photographic emulsion may have a regular crystal structure, e.g., a cubic or octahedral structure, an irregular crystal structure, e.g., a spherical or plate-like structure, or a composite structure thereof. In addition, silver halide particles composed of those having different crystal structures may be used.

Further, photographic emulsions wherein at least 50% of the total projected area of silver halide particles is silver halide particles having a length/thickness ratio of 8 or more may be employed.

The inner portion (core) and the surface layer (shell) of the silver halide particles may be different in phase or may be of uniform phase. The silver halide particles may be those in which a latent image is formed mainly on the surface thereof or those in which a latent image is formed mainly in the interior thereof.

Photographic emulsions used in the present invention can be prepared in any suitable manner, e.g., by the methods as described in P. Glafkides, *Chimie et Physique Photographique,* Paul Montel (1967), G. F. Duffin, *Photographic Emulsion Chemistry,* The Focal Press (1966), and V. L. Zelikman et al., *Making and Coating Photographic* Emulsion, The Focal Press (1964). That is, any of an acid process, a neutral process, an ammonia process, etc., can be employed.

Soluble silver salts and soluble halogen salts can be reacted by techniques such as a single jet process, a double jet process, and a combination thereof. In addition, there can be employed a method (reversal mixing process) in which silver halide particles are formed in the presence of an excess of silver ions.

As one system of the double jet process, a controlled double jet process in which the pAg in the liquid phase where silver halide is formed is maintained at a predetermined level can be employed. This process can produce a silver halide emulsion in which the crystal form is regular and the grain size is nearly uniform.

Two or more kinds of silver halide emulsions which are prepared separately may be used as a mixture.

The formation or physical ripening of silver halide particles may be carried out in the presence of cadmium salts, zinc salts, lead salts, thallium salts, iridium salts or complex salts thereof, rhodium salts or complex salts thereof, iron salts or complex salts thereof, and the like.

Silver halide emulsions are usually chemically sensitized. For this chemical sensitization, for example, the methods as described in H. Frieser ed., *Die Grendlagen der Photographischen Prozesse mit Silberhalogeniden,* Akademische Verlagsgesellschaft, pages 675 to 734 (1968) can be used. Namely, a sulfur sensitization process using active gelatin or compounds (e.g., thiosulfates, thioureas, mercapto compounds, rhodanines, etc.) containing sulfur capable of reacting with silver; a reduction sensitization process using reducing substances (e.g., stannous salts, amines, hydrazine derivatives, formamidinesulfinic acid, silane compounds, etc.); a noble metal sensitization process using noble metal compounds (e.g., complex salts of Group VIII metals in the Periodic Table, such as Pt, Ir and Pd, etc., as well as gold complex salts); and so forth can be applied alone or in combination with each other.

Photographic emulsions used in the present invention may include various compounds for the purpose of preventing fog formation or stabilizing photographic performance in the photographic light-sensitive materials during the production, storage or photographic processing thereof. For example, those compounds known as antifoggants or stabilizers can be incorporated, including azoles such as benzothiazolium salts, nitroimidazoles, triazoles, benzotriazoles, benzimidazoles (particularly nitro substituted or halogen substituted ones), etc.; heterocyclic mercapto compounds such as mercaptothiazoles, mercaptobenzothiazoles, mercaptobenzimidazoles, mercaptothiadiazoles, mercaptotetrazoles (particularly 1-phenyl-5-mercaptotetrazole), mercaptopyrimidines, etc.; the above described heterocyclic mercapto compounds having a water-soluble group such as a carboxy group, a sulfo group, etc.; thioketo compounds such as oxazolinethione, etc.; azaindenes such as tetraazaindenes (particularly 4-hydroxy-substituted (1,3,3a,7)tetraazaindenes), etc.; benzenethiosulfonic acids; benzenesulfinic acids; and the like.

In photographic emulsion layers or other hydrophilic colloid layers of the photographic light-sensitive material of the present invention there can be incorporated various surface active agents as coating aids or for other various purposes, e.g., prevention of charging, improvement of slipping properties, acceleration of emulsification and dispersion, prevention of adhesion, and improvement of photographic characteristics (particularly development acceleration, high contrast and sensitization), etc.

The photographic emulsion layer of the photographic light-sensitive material of the present inventon may contain compounds such as polyalkylene oxide or its ether, ester, amine or like derivatives, thioether compounds, thiomorpholines, quaternary ammonium salt compounds, urethane derivatives, urea derivatives, imidazole derivatives, and 3-pyrazolidones for the purpose of increasing sensitivity or contrast, or of accelerating development.

In photographic emulsion layers or other hydrophilic colloid layers of the photographic light-sensitive material of the present invention there can be incorporated water-insoluble or sparingly soluble synthetic polymer dispersions for the purpose of improving dimensional stability, etc. Synthetic polymers which can be used include homo- or copolymers of alkyl acrylates or methacrylates, alkoxyalkyl acrylates or methacrylates, glycidyl acrylates or methacrylates, acrylamides or methacrylamides, vinyl esters (e.g., vinyl acetate), acrylonitriles, olefins, styrenes, etc., and copolymers of the foregoing monomers and acrylic acids, methacrylic acids, $\alpha,\beta$-unsaturated dicarboxylic acids, hydroxyalkyl acrylates or methacrylates, sulfoalkyl acrylates or methacrylates, and styrenesulfonic acids.

In photographic processing of layers composed of photographic emulsions in the photographic light-sensitive material of the present invention, any known procedures and known processing solutions, e.g., those described in *Research Disclosure,* No. 176, pages 28–30 (RD-17643), can be used. This photographic processing may be a photographic processing (color photographic process) to form dye images, depending on the purpose. The processing temperature is usually chosen from between 18° C. and 50° C., although it may be lower than 18° C. or higher than 50° C.

As a specific developing technique, there may be used a method in which a developing agent is incorporated in a photographic light-sensitive material, for example, in an emulsion layer, and the photographic light-sensitive material is developed by treating in an alkali aqueous solution. Of developing agents, hydrophobic ones can be incorporated into the emulsion layer by various techniques, e.g., by the methods as described in *Research Disclosure*, No. 169 (RD-16928), U.S. Pat. No. 2,739,890, British Pat. No. 813,253, West German Pat. No. 1,547,763, etc. This photographic processing may be performed in combination with a silver salt stabilizing treatment using thiocyanic acid salts.

Any fixing solutions which are generally used can be used in the present invention. As fixing agents, thiosulfuric acid salts and thiocyanic acid salts, and in addition, organic sulfur compounds which are known effective as fixing agents can be used. These fixing solutions may contain water-soluble aluminum salts as hardeners.

Formation of dye images can be achieved by conventional methods. For example, a negative-positive method (described in, for example, *Journal of the Society of Motion Picture and Television Engineers*, Vol. 61, pages 667 to 701 (1953)) can be employed.

Color developing solutions are usually alkaline aqueous solutions containing color developing agents. As these color developing agents, known primary aromatic amine developing agents, e.g., phenylenediamines such as 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline, and 4-amino-3-methyl-N-ethyl-N-$\beta$-methoxyethylaniline, etc., can be used.

The color developing solutions can further contain pH buffering agents, developing inhibitors or antifogging agents, etc. In addition, if desired, the color developing solution can also contain water softeners, preservatives, organic solvents, developing accelerators, dye forming couplers, competing couplers, fogging agents, auxiliary developing agents, viscosity-imparting agents, polycarboxylic acid type chelating agents, antioxidizing agents, and the like.

After color development, the photographic emulsion layer is usually bleached. This bleach processing may be performed simultaneously with a fix processing, or they may be performed independently.

Bleaching agents which can be used include compounds of polyvalent metals, e.g., iron (III), cobalt (III), chromium (VI), and copper (II), peracids, quinones and nitroso compounds. For example, ferricyanides, dichromates; organic complex salts of iron (III) or cobalt (III), e.g., complex salts of aminopolycarboxylic acids (e.g., ethylenediaminetetraacetic acid, nitrilotriacetic acid, 1,3-diamino-2-propanoltetraacetic acid, etc.) or organic acids (e.g., citric acid, tartaric acid, malic acid, etc.); persulfates; permanganates; nitrosophenol, etc., can be used. Of these compounds, potassium ferricyanide, iron (III) sodium ethylenediaminetetraacetate, and iron (III) ammonium ethylenediaminetetraacetate are particularly useful. Ethylenediaminetetraacetic acid iron (III) complex salts are useful in both an independent bleaching solution and a monobath bleach-fixing solution.

The photographic emulsion used in the present invention can also be spectrally sensitized with methane dyes or other dyes.

These sensitizing dyes can be employed individually, and can also be employed in combination. A combination of sensitizing dyes is often used particularly for the purpose of supersensitization.

The present invention is also applicable to a multilayer multicolor photographic material containing layers sensitive to at least two different spectral wavelength ranges on a support. A multilayer natural color photographic material generally possesses at least one red-sensitive silver halide emulsion layer, at least one green-sensitive silver halide emulsion layer and at least one blue-sensitive silver halide emulsion layer, respectively, on a support. The order of these layers can be varied, if desired. Ordinarily, a cyan forming coupler is present in a red-sensitive emulsion layer, a magenta forming coupler is present in a green-sensitive emulsion layer and a yellow forming coupler is present in a blue-sensitive emulsion layer, respectively. However, if desired, a different combination can be employed.

The photographic light-sensitive material of the present invention may contain inorganic or organic hardeners in the photographic emulsion layers and other hydrophilic colloid layers thereof. For example, chromium salts (e.g., chromium alum, chromium acetate, etc.), aldehydes (e.g., formaldehyde, glyoxal, glutaraldehyde, etc.), N-methylol compounds (e.g., dimethylolurea, methyloldimethylhydantoin, etc.), dioxane derivatives (e.g., 2,3-dihydroxydioxane, etc.), active vinyl compounds (e.g., 1,3,5-triacryloyl-hexahydro-s-triazine, 1,3-vinylsulfonyl-2-propanol, etc.), active halogen compounds (e.g., 2,4-dichloro-6-hydroxy-s-triazine, etc.), and mucohalogenic acids (e.g., mucochloric acid, mucophenoxychloric acid, etc.) can be used alone or in combination with each other.

In the photographic light-sensitive material of the invention, when dyes, ultraviolet ray absorbing agents, and the like are incorporated in the hydrophilic colloid layers, they may be mordanted with cationic polymers, etc.

The photographic light-sensitive material of the present invention may contain therein hydroquinone derivatives, aminophenol derivatives, gallic acid derivatives, ascorbic acid derivatives, etc., as color fog preventing agents.

The hydrophilic colloid layers of the photographic light-sensitive material of the present invention can contain ultraviolet ray absorbing agents. For example, benzotriazole compounds substituted with aryl groups, 4-thiazolidone compounds, benzophenone compounds, cinnamic acid ester compounds, butadiene compounds, benzoxazole compounds, ultraviolet ray absorbing polymers, etc., can be employed. These ultraviolet ray absorbing agents can also be mordanted in a specific layer(s), if desired.

The photographic light-sensitive material of the present invention may contain water-soluble dyes in the hydrophilic colloid layers thereof as filter dyes or for various purposes, e.g., irradiation prevention. Examples of such dyes include oxonol dyes, hemioxonol dyes, styryl dyes, merocyanine dyes, cyanine dyes, and azo dyes. In particular, oxonol dyes, hemioxonol dyes and merocyanine dyes are useful.

In carrying out the present invention, known color fading preventing agents described below can be used together. Color image stabilizers can be used alone or in combination with each other. Typical known color fading preventing agents include hydroquinone derivatives, gallic acid derivatives, p-alkoxyphenols, p-oxyphenol derivatives and bisphenols, etc.

The present invention will now be explained in greater detail with reference to the following examples, but the present invention should not be construed as being limited thereto. Unless otherwise indicated, all percents are by weight.

EXAMPLE 1

Samples RA and RB:

15.1 g of Comparison Coupler A shown below or 15.1 g of Comparison Coupler B shown below was dissolved with 20 ml of trioctyl phosphate, 5 ml of tricresyl phosphate and 10 ml of ethyl acetate. The resulting solution was added to 100 g of a 10% aqueous gelatin solution containing 0.2 g of sodium di-sec-butylnaphthalenesulfonate, and the mixture was stirred and dispersed by means of a homogenizer to prepare a dispersion. The dispersion thus prepared was mixed with 300 g of a green-sensitive silver chlorobromide gelatin emulsion (containing 13.5 g of silver, and having a bromide content of 45 mol % and a chloride content of 55 mol %). There were added thereto 0.3 g of sodium dodecylbenzenesulfonate as a coating aid and 0.2 g of 2-hydroxy-4,6-dichloro-s-triazine as a hardener. The mixture was coated on a cellulose triacetate support in a silver coated amount of 0.67 g/m² to form an emulsion layer. Further, a gelatin coating solution was applied to the emulsion layer as a protective layer at a coverage of 1 g of gelatin per square meter, and dried. The photographic light-sensitive materials thus prepared using Comparison Couplers A and B were designated Samples RA and RB, respectively.

Comparison Coupler A

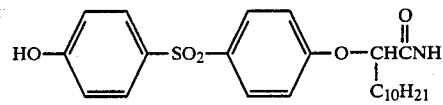
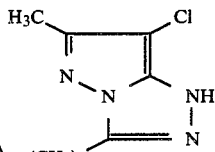

Comparison Coupler B

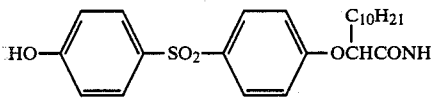
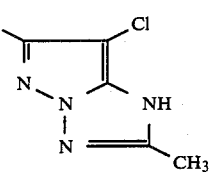

Samples 1 and 2:

Samples 1 and 2 were prepared in the same manner as described for Film RA above except using 23.7 g of Couplers 14 and 16 according to the present invention, respectively, in place of Comparison Coupler A.

Films RA, 1, RB and 2 described above were exposed to light using a sensitometer at 1,000 lux·1 sec and subjected to the following development processing.

| Processing Step | Temperature | Time |
|---|---|---|
| Development | 33° C. | 3 min |
| Bleach-Fixing | 33° C. | 1 min 30 sec |
| Washing | 28 to 35° C. | 3 min |
| Drying | | |

The processing solutions used had the following compositions.

| Developing Solution | |
|---|---|
| Trisodium Nitrilotriacetate | 2.0 g |
| Benzyl Alcohol | 15 ml |
| Diethylene Glycol | 10 ml |
| Sodium Sulfite | 2.0 g |

| -continued | |
|---|---|
| Developing Solution | |
| Potassium Bromide | 0.5 g |
| Hydroxylamine Sulfate | 3.0 g |
| 4-Amino-3-methyl-N—ethyl-N—[β-(methanesulfonamido)ethyl]-p-phenylenediamine Sulfate | 5.0 g |
| Sodium Carbonate (monohydrate) | 30 g |
| Water to make | 1 liter |
| | (pH: 10.1) |

| Bleach-Fixing Solution | |
|---|---|
| Ammonium Thiosulfate (70 wt %) | 150 ml |
| Sodium Sulfite | 15 g |
| Ammonium Ethylenediaminetetraacetato Iron (III) | 55 g |
| Disodium Ethylenediaminetetraacetate | 4 g |
| Water to make | 1 liter |
| | (pH: 6.9) |

The maximum densities ($D_{max}$) of the resulting dye images after color development processing were measured using a Macbeth transmission densitometer with a Status AA filter. The results thus obtained are shown in Table 1 below.

Further, the light fastness of each sample in which magenta dye images were formed was determine using a fluorescent lamp fading tester. Each sample was irradiated at 15,000 lux for 2 weeks and then the remaining dye density in an area having an initial density of 2.0 was measured and the density difference ($\Delta D$) based on color fading was determined. The results thus obtained are also shown in Table 1 below.

TABLE 1

| Sample | Coupler | Relative* Sensitivity | $D_{max}$ | Color Fading $\Delta D$ |
|---|---|---|---|---|
| 1 (Invention) | 14 | 52 | 3.50 | 0.90 |
| RA (Comparison) | A | 100 | 3.34 | 1.08 |
| 2 (Invention) | 16 | 47 | 3.26 | 0.16 |
| RB (Comparison) | B | 100 | 3.02 | 0.40 |

*Relative sensitivity is the value of the exposure amount required to obtain an optical density of fog + 0.2 and is shown by taking Samples RA and RB as 100 as the standard for Sample 1 and 2, respectively.

It is apparent from the results shown in Table 1 above that the couplers having a fluorine-substituted carbon-amido group as a group capable of being released upon coupling not only provide extremely high sensitivity and high $D_{max}$ but also provide magenta dyes having good light fastness in comparison with the comparison couplers having a chlorine atom as a group capable of being released upon coupling.

EXAMPLE 2

Samples 3 to 10 were prepared in the same manner as described for Sample RA in Example 1 except that 200 g of a green-sensitive silver iodobromide emulsion (containing 9 g of silver, and having an iodide content of 6 mol % and a bromide content of 94 mol %) was used and 21 millimols of the coupler according to the present invention as shown in Table 2 below was used in place of Comparative Coupler A and the mixture was coated on the support in a silver coated amount of 0.45 g/m². These samples were subjected to the same development processing as described in Example 1 and the maximum density of each sample thus processed was measured. The molar ratio of silver and coupler (Ag/Cp) was 4 in each sample. The results thus obtained are shown in Table 2.

TABLE 2

| Sample | Coupler | Maximum Density |
|---|---|---|
| RA | A | 2.19 |
| 3 | 2 | 2.41 |
| 4 | 6 | 2.49 |
| 5 | 8 | 2.47 |
| 6 | 12 | 2.56 |
| 7 | 17 | 2.62 |
| 8 | 18 | 2.66 |
| 9 | 22 | 2.65 |
| 10 | 24 | 2.63 |

From the results shown in Table 2 above it is apparent that the couplers according to the present invention exhibit high color forming property.

EXAMPLE 3

12 g of Comparison (magenta) Coupler A as described in Example 1 was dissolved in a mixture of 24 ml of tricresyl phosphate and 24 ml of ethyl acetate and the resulting solution was dispersed in 80 g of a 10% aqueous gelatin solution containing 8 ml of a 1% aqueous solution of sodium dodecylbenzenesulfonate. The dispersion thus prepared was mixed with 145 g of a green-sensitive silver chlorobromide emulsion (having a bromide content of 70 mol %) and there was added thereto sodium dodecylbenzenesulfonate as a coating aid. The resulting coating solution was used as the third layer of a color photographic light-sensitive material having the layer composition as shown in Table 3 below to prepare Color Photographic Light-Sensitive Material R-1 for comparison. In Table 3 below the coating amounts are set forth in mg/m².

TABLE 3

Support:
Paper support, both surfaces of which were laminated with polyethylene

First Layer: Blue-Sensitive Layer

| | |
|---|---|
| Silver chlorobromide emulsion (silver bromide: 80 mol %; silver: 400 mg/m²) | |
| Gelatin | 1,200 mg/m² |
| Yellow coupler*⁴ | 300 mg/m² |
| Coupler solvent*⁵ | 300 mg/m² |

Second Layer: Interlayer

| | |
|---|---|
| Gelatin | 1,000 mg/m² |

Third Layer: Green-Sensitive Layer

TABLE 3-continued

| | |
|---|---|
| Silver chlorobromide emulsion (silver bromide: 70 mol %; silver: 300 mg/m²) | |
| Gelatin | 1,000 mg/² |
| Magenta coupler (as shown in Table 4 below; 0.3 mmol/m²) | |
| Coupler solvent*⁶ | 200 mg/m² |

Fourth Layer: Interlayer

| | |
|---|---|
| Gelatin | 1,200 mg/m² |
| Ultraviolet light-absorbing agent*³ | 1,000 mg/m² |
| Ultraviolet light-absorbing agent solvent | 300 mg/m² |

Fifth Layer: Red-Sensitive Layer

| | |
|---|---|
| Silver chlorobromide emulsion (silver bromide; 50 mol %; silver: 300 mg/m²) | |
| Gelatin | 1,000 mg/m² |
| Cyan coupler*¹ | 400 mg/m² |
| Coupler solvent*² | 300 mg/m² |

Sixth Layer: Protective Layer

| | |
|---|---|
| Gelatin | 1,000 mg/m² |

*¹Cyan coupler: 2-[α-(2,4-Di-tert-pentylphenoxy)-butanamido]-4,6-dichloro-5-methyl-phenol
*²Solvent: Dibutyl phthalate
*³Ultraviolet light-absorbing agent: 2-(2-Hydroxy-3-sec-butyl-5-tert-butyl-phenyl)-benzotriazole
*⁴Yellow coupler: α-Pivaloyl-α-(2,4-dioxo-5,5'-dimethyloxazolidin-3-yl)-2-chloro-5-[α-(2,4-di-tert-pentylphenoxy)-butanamido]acetanilide
*⁵Solvent: Dioctyl butyl phosphate
*⁶Solvent: Tricresyl phosphate Samples 11 to 15 according to the present invention were prepared in the same manner as described for Sample R-1 except that each of the magenta couplers according to the present invention as shown in Table 4 below was used in place of Comparison Magenta Coupler A in the preparation of the coating solution for the third layer.

These samples were exposed to light and processed in the same manner as described in Example 1 to form color images. The optical density of the magenta dye images was measured and the results thus obtained are shown in Table 4 below.

Further, the samples thus processed were subjected to a fading test (ΔD) using a fluorescent lamp fading tester (20,000 lux) for 4 weeks. The results thus obtained are also shown in Table 4.

TABLE 4

| Sample | | Coupler Used | $D_{max}$ (G) | ΔD (2.0) |
|---|---|---|---|---|
| R-1 | (Comparison) | A | 1.85 | 0.83 |
| 11 | (Present Invention) | 14 | 2.37 | 0.26 |
| 12 | (Present Invention) | 17 | 2.62 | 0.15 |
| 13 | (Presnet Invention) | 4 | 2.55 | 0.15 |
| 14 | (Present Invention) | 7 | 2.47 | 0.17 |
| 15 | (Present Invention) | 22 | 2.58 | 0.16 |

From the results shown in Table 4 above it is seen that the effects on improvements in the color forming property and fastness according to the present invention are also obtained in these samples. More specifically, when the maximum magenta density, i.e., $D_{max}$ (G) is compared with Comparison Sample R-1 and Samples 11 to 15 according to the present invention, it is apparent that Samples 11 to 15 provide higher values than Sample R-1. Further, the decrease in density in the area having the initial density of 2.0, i.e., ΔD (2.0), due to the irradiation for a long period of time was small in the samples wherein the couplers according to the present invention were used as compared with the comparison sample. This indicates excellent fastness to light according to the present invention.

EXAMPLE 4

On a polyethylene terephthalate film support were coated layers having the compositions set forth below to prepare a multilayer color photographic light-sensitive material.

First Layer: Antihalation Layer
A gelatin layer containing black colloidal silver
Second Layer: Intermediate Layer
A gelatin layer containing a dispersion of 2,5-di-tert-octylhydroquinone
Third Layer: First Red-Sensitive Emulsion Layer
A silver iodobromide emulsion (iodide content: 5 mol %), silver coated amount: 1.6 g/m$^2$

| | |
|---|---|
| Sensitizing Dye I | $4.5 \times 10^{-4}$ mol per mol of silver |
| Sensitizing Dye II | $1.5 \times 10^{-4}$ mol per mol of silver |
| Coupler EX-1 | 0.04 mol per mol of silver |
| Coupler EX-3 | 0.003 mol per mol of silver |
| Coupler EX-9 | 0.0006 mol per mol of silver |

Fourth Layer: Second Red-Sensitive Emulsion Layer
A silver iodobromide emulsion (iodide content: 10 mol %), silver coated amount: 1.4 g/m$^2$

| | |
|---|---|
| Sensitizing Dye I | $3 \times 10^{-4}$ mol per mol of silver |
| Sensitizing Dye II | $1 \times 10^{-4}$ mol per mol of silver |
| Coupler EX-1 | 0.002 mol per mol of silver |
| Coupler EX-2 | 0.02 mol per mol of silver |
| Coupler EX-3 | 0.0016 mol per mol of silver |

Fifth Layer: Intermediate Layer
Same as the Second Layer
Sixth Layer: First Green-Sensitive Emulsion Layer
A silver iodobromide emulsion (iodide content: 4 mol %), silver coated amount: 0.6 g/m$^2$

| | |
|---|---|
| Sensitizing Dye III | $5 \times 10^{-4}$ mol per mol of silver |
| Sensitizing Dye IV | $2 \times 10^{-4}$ mol per mol of silver |
| Coupler EX-4 | 0.05 mol per mol of silver |
| Coupler EX-5 | 0.008 mol per mol of silver |
| Coupler EX-9 | 0.0015 mol per mol of silver |

Seventh Layer: Second Green-Sensitive Emulsion Layer
A silver iodobromide emulsion (iodide content: 8 mol %), silver coated amount: 0.65 g/m$^2$

| | |
|---|---|
| Sensitizing Dye III | $3 \times 10^{-4}$ mol per mol of silver |
| Sensitizing Dye IV | $1.2 \times 10^{-4}$ mol per mol of silver |
| Coupler EX-7 | 0.017 mol per mol of silver |
| Coupler EX-6 | 0.003 mol per mol of silver |
| Coupler EX-10 | 0.0003 mol per mol of silver |

Eighth Layer: Yellow Filter Layer
A gelatin layer containing yellow colloidal silver and a dispersion of 2,5-di-tert-octylhydroquinone
Ninth Layer: First Blue-Sensitive Emulsion Layer
A silver iodobromide emulsion (iodide content: 6 mol %), silver coated amount: 0.7 g/m$^2$

| | |
|---|---|
| Coupler EX-8 | 0.25 mol per mol of silver |
| Coupler EX-9 | 0.015 mol per mol of silver |

Tenth Layer: Second Blue-Sensitive Emulsion Layer
A silver iodobromide emulsion (iodide content: 6 mol %), silver coated amount: 0.6 g/m$^2$

| | |
|---|---|
| Coupler EX-8 | 0.06 mol per mol of silver |

Eleventh Layer: First Protective Layer
A gelatin layer containing silver iodobromide (iodide content: 1 mol %, average particle size: 0.07 μ), silver coated amount: 0.5 g/m$^2$ and a dispersion of Ultraviolet Ray Absorbing Agent UV-1.
Twelfth Layer: Second Protective Layer
A gelatin layer containing polymethyl methacrylate particles (having a diameter of about 1.5 μ)

Gelatin Hardener H-1 and a surface active agent were incorporated into each of the layers in addition to the above described components.

The sample thus prepared was imagewise exposed to light and subjected to development processing as described below. A color negative film having good color separation was obtained. This negative film was printed onto a color paper to achieve improved color reproduction.

The compounds used for preparing the sample were as follows:

Coupler EX-1

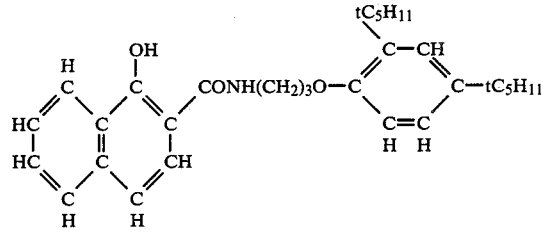

Coupler EX-2

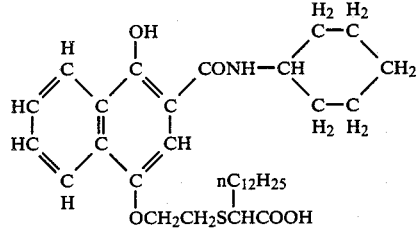

Coupler EX-3

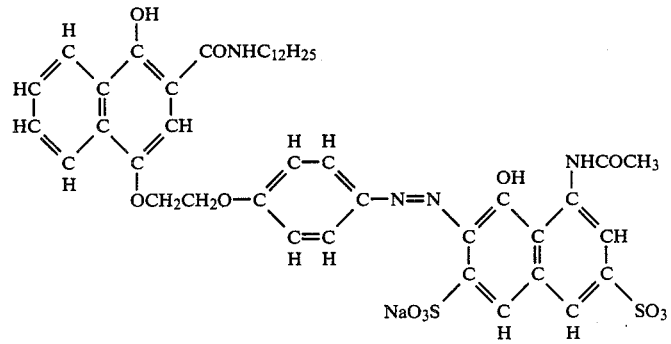

Couplers EX-4 and EX-7

Coupler 16 according to the present invention

Coupler EX-5

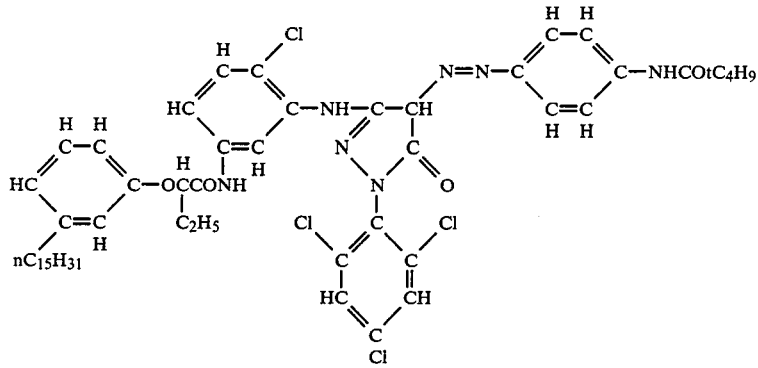
Coupler EX-6
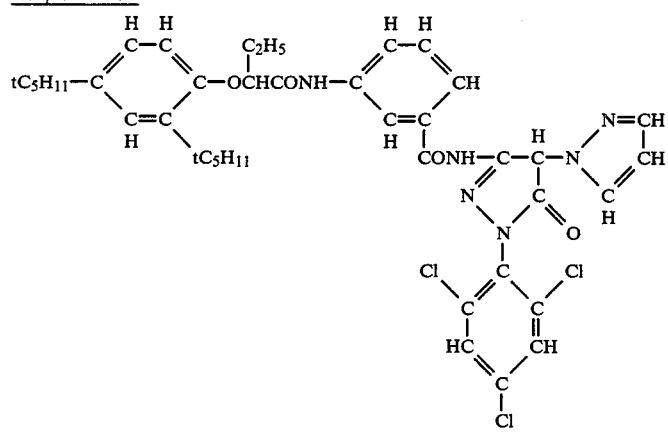
Coupler EX-8
Coupler EX-9
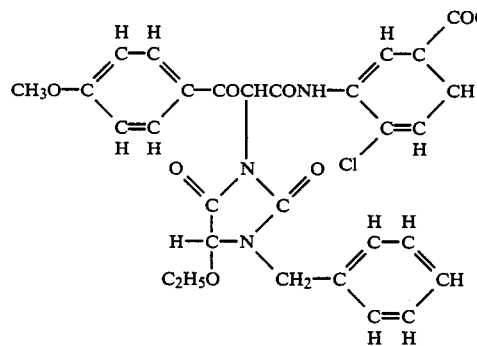
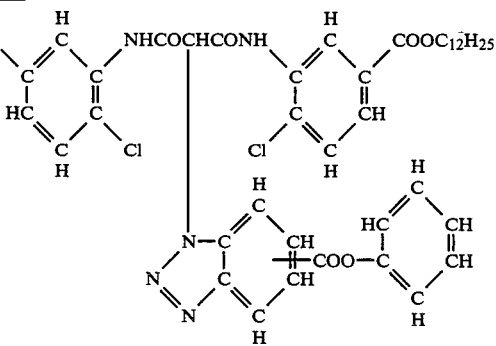
Coupler EX-10
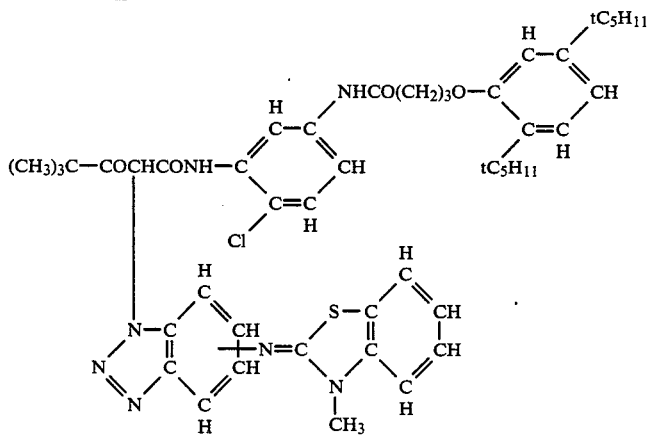
Gelatin Hardener H-1          Ultraviolet Ray Absorbing Agent UV-1

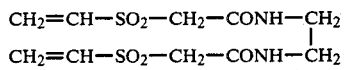
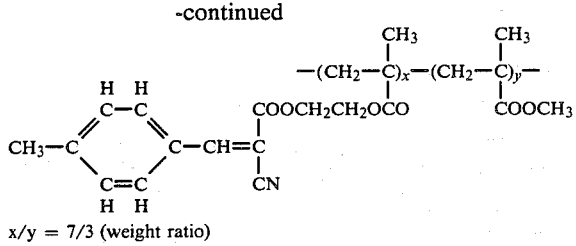
x/y = 7/3 (weight ratio)
Sensitizing Dye I
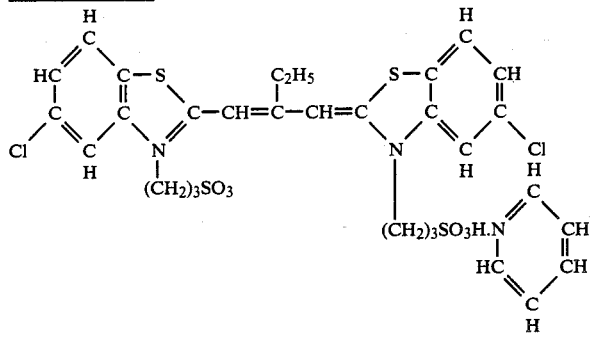
Sensitizing Dye II
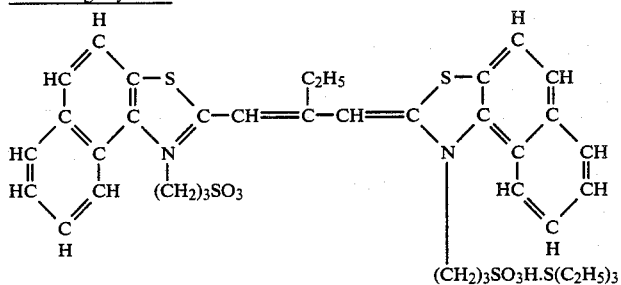
Sensitizing Dye III
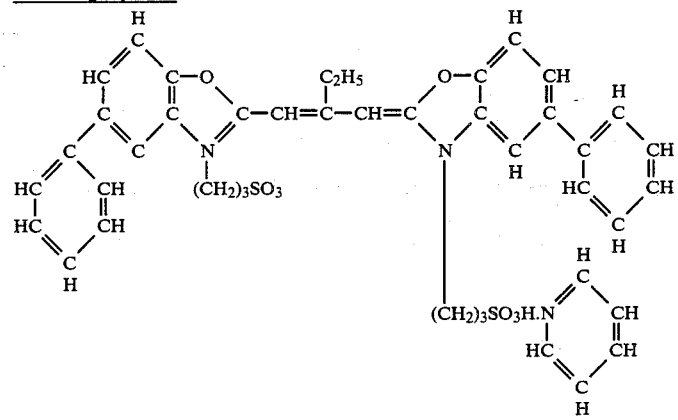
Sensitizing Dye IV
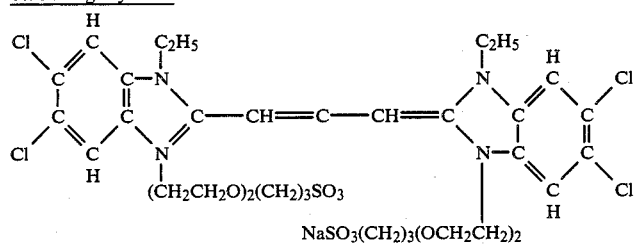
The development processing was carried out at 38° C. according to the following processing steps.

| 1. Color Development | 3 min & 15 sec |
| 2. Bleaching | 6 min & 30 sec |
| 3. Washing with Water | 3 min & 15 sec |
| 4. Fixing | 6 min & 30 sec |
| 5. Washing with Water | 3 min & 15 sec |
| 6. Stabilizing | 3 min & 15 sec |

The composition of each processing solution used in the above described processing is as follows.

| Color Developing Solution | |
| --- | --- |
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N—Ethyl-N—$\beta$-hydroxyethylamino)-2-methylaniline Sulfate | 4.5 g |
| Water to make | 1 liter |

| Bleaching Solution | |
| --- | --- |
| Ammonium Bromide | 160.0 g |
| Aqueous Ammonia (28%) | 25.0 ml |
| Sodium Ethylenediaminetetraacetato-Fe (III) | 130.0 g |
| Glacial Acetic Acid | 14.0 ml |
| Water to make | 1 liter |

| Fixing Solution | |
| --- | --- |
| Sodium Tetrapolyphosphate | 2.0 g |
| Sodium Sulfite | 4.0 g |
| Ammonium Thiosulfate Aqueous Solution (70%) | 175.0 ml |
| Sodium Bisulfite | 4.6 g |
| Water to make | 1 liter |

| Stabilizing Solution | |
| --- | --- |
| Formalin (40%) | 8.0 ml |
| Water to make | 1 liter |

EXAMPLE 5

On a triacetyl cellulose support provided with a subbing layer were coated in order the emulsion layers and subsidiary layers as described below to prepare Sample A.

First Layer: Low-Sensitive Red-Sensitive Emulsion Layer 100 g of a cyan coupler, i.e., 2-(heptafluorobutyramido)-5-[2'-(2",4"-di-tert-aminophenoxy)-butyramido]-phenol was dissolved in 100 ml of tricresyl phosphate and 100 ml of ethyl acetate and stirred at a high speed together with 1 kg of a 10% aqueous gelatin solution to prepare an emulsion. Then, 500 g of the emulsion thus obtained was mixed with 1 kg of a low-sensitive red-sensitive silver iodobromide emulsion (containing 70 g of silver and 60 g of gelatin, and having an iodide content of 6 mol % and the grain size distribution wherein 81% of the total number of silver halide grains had a size within the range of the mean grain size ±40%), and the resulting mixture was then coated at a dry thickness of 2 $\mu$ (silver amount: 0.5 g/m$^2$)

Second Layer: Medium-Sensitive Red-Sensitive Emulsion Layer 100 g of a cyan coupler, i.e., 2-(heptafluorobutyramido)-5-[2'-(2",4"-di-tert-aminophenoxy)-butyramido]-phenol was dissolved in 100 ml of tricresyl phosphate and, 100 ml of ethyl acetate and stirred at a high speed together with 1 kg of a 10% aqueous gelatin solution to prepare an emulsion. Then, 1 kg of the emulsion thus obtained was mixed with 1 kg of a medium-sensitive red-sensitive silver iodobromide emulsion (containing 70 g of silver and 60 g of gelatin, and having an iodide content of 6 mol % and 76% of the grain size distribution as defined in the emulsion of First Layer), and the resulting mixture was then coated at a dry thickness of 1$\mu$ (silver amount: 0.4 g/m$^2$).

Third Layer: High-Sensitive Red-Sensitive Emulsion Layer 100 g of a cyan coupler, i.e., 2-(heptafluorobutyramido)-5-[2'-(2",4"-di-tert-aminophenoxy)-butyramido]-phenol was dissolved in 100 ml of tricresyl phosphate and 100 ml of ethyl acetate and stirred at a high speed. together with 1 kg of a 10% aqueous gelatin solution to prepare an emulsion. Then, 1 kg of the emulsion thus obtained was mixed with 1 kg of a high-sensitive red-sensitive silver iodobromide emulsion (containing 70 g of silver and 60 g of gelatin, and having an iodide content of 6 mol % and 78% of the grain size distribution as defined above), and the resulting mixture was then coated at a dry thickness of 1 $\mu$ (silver amount: 0.4 g/m$^2$).

Fourth Layer: Intermediate Layer 2,5-Di-tert-octylhydroquinone was dissolved in 100 ml of dibutyl phthalate and 100 ml of ethyl acetate, and stirred at a high speed together with 1 kg of a 10% aqueous gelatin solution to prepare an emulsion. Then, 1 kg of the emulsion thus obtained was mixed with 1 kg of a 10% aqueous gelatin solution, and the resulting mixture was coated at a dry thickness of 1$\mu$.

Fifth Layer: Low-Sensitive Green-Sensitive Emulsion Layer

An emulsion was prepared in the same manner as described in the preparation of the emulsion for First Layer except that a magenta coupler, i.e., 1-(2,4,6-trichlorophenyl)-3-[3-(2,4-di-tert-amylphenoxyacetamido)-benzamido]-5-pyrazolone, was used in place of the cyan coupler. Then, 500 g of the emulsion thus obtained was mixed with 1 kg of a green-sensitive, low-sensitive silver iodobromide emulsion (containing 70 g of silver and 60 g of gelatin, and having an iodine content of 5.2 mol % and 81% of the grain size distribution as defined above), and the resulting mixture was coated at a dry thickness of 2.0$\mu$ (silver amount: 0.7 g/m$^2$).

Sixth Layer: Medium-Sensitive Green-Sensitive Emulsion Layer

An emulsion was prepared in the same manner as described in the preparation of the emulsion for First Layer except that a magenta coupler, i.e., 1-(2,4,6-trichlorophenyl)- 3-[3-(2,4-di-tert-amylphenoxyacetamido)-benzamido]-5-pyrazolone, was used in place of the cyan coupler. Then, 1 kg of the emulsion thus obtained was mixed with 1 kg of a green-sensitive medium-sensitive silver iodobromide emulsion (containing 70 g of silver and 60 g of gelatin, and having an iodine content of 5.2 mol % and 75% of the grain size distribution as defined above), and the resulting mixture was coated at a dry thickness of 1$\mu$ (silver amount: 0.35 g/m$^2$).

Seventh Layer: High-Sensitive Green-Sensitive Emulsion Layer

An emulsion was prepared in the same manner as described in the preparation of the emulsion for First Layer except that a magenta coupler, i.e., Coupler 16 according to the present invention, was used in place of the cyan coupler. Then, 1 kg of the emulsion thus obtained was mixed with 1 kg of a green-sensitive high-sensitive silver iodobromide emulsion (containing 70 g of silver and 60 g of gelatin, and having an iodine content of 5.2 mol % and 75% of the grain size distribution as defined above), and the resulting mixture was coated at a dry thickness of 1μ (silver amount: 0.25 g/m$^2$).

Eighth Layer: Intermediate Layer 1 kg of the emulsion used in the preparation of Fourth Layer was mixed with 1 kg of a 10% aqueous gelatin solution and coated at a dry thickness of 1μ.

Ninth Layer: Yellow Filter Layer

An emulsion containing yellow colloidal silver was coated at a dry thickness of 1μ.

Tenth Layer: Low-Sensitive Blue-Sensitive Emulsion Layer

An emulsion was prepared in the same manner as described in the preparation of the emulsion for First Layer except that a yellow coupler, i.e., α-pivaloyl-α-(1-benzyl-5-ethoxy-3-hydantoinyl)-2-chloro-5-dodecyloxycarbonylacetanilide, was used in place of the cyan coupler. Then, 1 kg of the emulsion thus obtained was mixed with 1 kg of a blue-sensitive low-sensitive silver iodobromide emulsion (containing 70 g of silver and 60 g of gelatin and having an iodine content of 5.5 mol % and 77% of the grain size distribution as defined above), and the resulting mixture was coated at a dry thickness of 2.0μ (silver amount: 0.6 g/m$^2$).

Eleventh Layer: Medium-Sensitive Blue-Sensitive Emulsion Layer

An emulsion was prepared in the same manner as described in the preparation of the emulsion for First Layer except that a yellow coupler, i.e., α-pivaloyl-α-(1-benzyl-5-ethoxy-3-hydantoinyl)-2-chloro-5-dodecyloxycarbonylacetanilide, was used in place of the cyan coupler. Then, 1 kg of the emulsion thus obtained was mixed with 1 kg of a blue-sensitive medium-sensitive silver iodobromide emulsion (containing 70 g of silver and 60 g of gelatin and having an iodine content of 5.5 mol % and 72% of the grain size distribution as defined above), and the resulting mixture was coated at a dry thickness of 1.0μ (silver amount: 0.5 g/m$^2$).

Twelfth Layer: High-Sensitive Blue-Sensitive Emulsion Layer

An emulsion was prepared in the same manner as described in the preparation of the emulsion for First Layer except that a yellow coupler, i.e., α-pivaloyl-α-(1-benzyl-5-ethoxy-3-hydantoinyl)-2-chloro-5-dodecyloxycarbonylacetanilide, was used in place of the cyan coupler. Then, 1 kg of the emulsion thus obtained was mixed with 1 kg of a blue-sensitive high-sensitive silver iodobromide emulsion (containing 70 g of silver and 60 g of gelatin and having an iodine content of 5.5 mol % and 72% of the grain size distribution as defined above), and the resulting mixture was coated at a dry thickness of 1.0μ (silver amount: 0.5 g/m$^2$).

Thirteenth Layer: Second Protective Layer 1 kg of the emulsion used in the preparation of Fourth Layer was mixed with 1 kg of a 10% aqueous gelatin solution and coated at a dry thickness of 2μ.

Fourteenth Layer: First Protective Layer

A 10% aqueous gelatin solution containing a fine grain silver iodobromide emulsion which had not been chemically sensitized (grain size: 0.15μ; 1 mol % silver iodobromide emulsion) was coated so that the amount of silver coated was 0.3 g/m$^2$ and the dry thickness was 1μ.

The multilayer film sample thus obtained was exposed to light through a wedge for sensitometry containing color patches for a color separation test and then subjected to the reversal processing described below. The reversal color film thus obtained had good saturation in the red and blue zones.

The development processing was carried out according to the following steps.

| Processing Steps | Time (min) | Temperature |
|---|---|---|
| First Development | 6 | 38 ± 0.3° C. |
| Washing with Water | 2 | " |
| Reversal | 2 | " |
| Color Development | 6 | " |
| Conditioning | 2 | " |
| Bleaching | 6 | " |
| Fixing | 4 | " |
| Washing with Water | 4 | " |
| Stabilizing | 1 | Ordinary Temperature |
| Drying | | |

The composition of each processing solution used in the above described processing is as follows.

| First Development Bath | |
|---|---|
| Water | 700 ml |
| Sodium Tetrapolyphosphate | 2 g |
| Sodium Sulfite | 20 g |
| Hydroquinone Monosulfonate | 30 g |
| Sodium Carbonate (monohydrate) | 30 g |
| 1-Phenyl-4-methyl-4-hydroxymethyl-3-pyrazolidone | 2.0 g |
| Potassium Bromide | 2.5 g |
| Potassium Thiocyanate | 1.2 g |
| Potassium Iodide (0.1% solution) | 2 ml |
| Water to make | 1,000 ml |

| Reversal Bath | |
|---|---|
| Water | 700 ml |
| 6 Na Salt of Nitrilo-N,N,N—trimethylenephosphonic Acid | 3 g |
| Stannous Chloride (dihydrate) | 1 g |
| p-Aminophenol | 0.1 g |
| Sodium Hydroxide | 8 g |
| Glacial Acetic Acid | 15 ml |
| Water to make | 1,000 ml |

| Color Development Bath | |
|---|---|
| Water | 700 ml |
| Sodium Tetrapolyphosphate | 2 g |
| Sodium Sulfite | 7 g |
| Sodium Tertiary Phosphate (12 hydrate) | 36 g |
| Potassium Bromide | 1 g |
| Potassium Iodide (0.1% solution) | 90 ml |
| Sodium Hydroxide | 3 g |
| Citrazinic Acid | 1.5 g |
| N—Ethyl-N—(β-methanesulfonamidoethyl)-3-methyl-4-aminoaniline Sulfate | 11 g |
| Ethylenediamine | 3 g |
| Water to make | 1,000 ml |

| Conditioning Bath | |
|---|---|
| Water | 700 ml |
| Sodium Sulfite | 12 g |
| Sodium Ethylenediaminetetraacetate (dihydrate) | 8 g |
| Thioglycerol | 0.4 ml |
| Glacial Acetic Acid | 3 ml |
| Water to make | 1,000 ml |

| Bleaching Bath | |
|---|---|
| Water | 800 ml |
| Sodium Ethylenediaminetetraacetate (dihydrate) | 2.0 g |
| Iron (III) Ammonium Ethylenediaminetetraacetate (dihydrate) | 120.0 g |
| Potassium Bromide | 100.0 g |
| Water to make | 1,000 ml |

| Fixing Bath | |
|---|---|
| Water | 800 ml |
| Ammonium Thiosulfate | 80.0 g |
| Sodium Sulfite | 5.0 |
| Sodium Bisulfite | 5.0 g |
| Water to make | 1,000 ml |

| Stabilizing Bath | |
|---|---|
| Water | 800 ml |
| Formalin (37 wt %) | 5.0 ml |
| Water to make | 1,000 ml |

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material comprising a support having thereon at least one silver halide emulsion layer, the photographic light-sensitive material containing a color image forming coupler comprising a nitrogen containing heterocyclic 5-membered ring-condensed-5-membered ring in which the coupling active position is substituted with the nitrogen atom of a carboxylic acid amido group containing at least one fluorine atom.

2. The silver halide photographic light-sensitive material as claimed in claim 1, wherein the color image forming coupler has a skeleton in which a 5-membered ring containing at least one nitrogen atom is condensed at the 1-position and the 5-position of a pyrazole ring and the coupling active position thereof is substituted with the nitrogen atom of an N-unsubstituted or substituted primary carboxylic acid amido group containing at least one fluorine atom.

3. The silver halide photographic light-sensitive material as claimed in claim 2, wherein the color image forming coupler is represented by the following general formula (I):

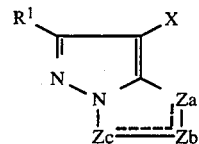

wherein X represents a group capable of being released upon coupling which is represented by general formula (II) described below; $R^1$ represents a hydrogen atom or a substituent; Za, Zb and Zc each represents an unsubstituted or substituted methine group, an unsubstituted or substituted methylene group, =N— or —NH—, one of the Za—Zb bond and the Zb—Zc bond being a double bond and the other being a single bond;

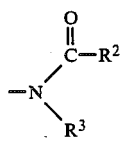

wherein $R^2$ represents a straight chain, branched chain or cyclic alkyl group, an aryl group or a heterocyclic group each of these groups being substituted with at least one fluorine atom; $R^3$ represents a hydrogen atom, an alkyl group, an aryl group, a heterocyclic group, an acyl group, an alkylsulfonyl group, an arylsulfonyl group, a carbamoyl group, a sulfamoyl group, an alkoxycarbonyl group or an aryloxycarbonyl group; and $R^2$ and $R^3$ may combine together with the nitrogen atom to form a 5-membered or 6-membered ring, which may be further condensed to a benzene ring or a heterocyclic ring.

4. The silver halide photographic light-sensitive material as claimed in claim 1, wherein the substituent represented by $R^1$ is a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group or an aryloxycarbonyl group.

5. The silver halide photographic light-sensitive material as claimed in claim 3, wherein the alkyl group, the aryl group or the heterocyclic group represented by $R^2$ is further substituted with a halogen atom other than a fluorine atom, a hydroxyl group, a cyano group, an aryl group, a heterocyclic group, a carboxyl group, an alkoxy group, an aryloxy group, an acylamino group, a sulfonamido group, an imido group, an alkoxycarbonyl group, an aryloxycarbonyl group, an alkylthio group, an arylthio group, an alkylsulfonyl group, an arylsulfonyl group, a carbamoyl group, a sulfamoyl group, an alkoxycarbonylamino group, an aryloxycarbonylamino group, a ureido group, an acyl group, an alkylamino group or an arylamino group.

6. The silver halide photographic light-sensitive material as claimed in claim 3, wherein the 5-membered or 6-membered ring formed by combining $R^2$ and $R^3$ together with the nitrogen atom is a cyclic imido group which has at least one fluorine atom on the ring or in a substituent attached to the ring, a 2-N-1,1-dioxo-3-(2H)-oxo-1,2-benzisothiazolyl group which has at least one fluorine atom on the ring or in a substituent attached to the ring, a group having at least one fluorine atom on the ring or in a substituent attached to the ring and being represented by the formula:

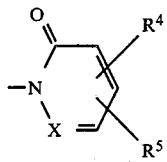

wherein X represents —CH= or —N=; and $R^4$ and $R^5$ each represents a hydrogen atom, a fluorine atom or a substituent selected from a halogen atom other than a fluorine atom, a cyano group, a nitro group, an alkyl group, an aryl group, a carboxyl group, an alkoxy group, an aryloxy group, an acylamino group, a sulfonamido group, a hydroxyl group, an imido group, an alkoxycarbonyl group, an aryloxycarbonyl group, an alkylthio group, an arylthio group, an alkylsulfonyl group, an arylsulfonyl group, a carbamoyl group, a sulfamoyl group, an alkoxycarbonylamino group, an aryloxycarbonylamino group, a ureido group, an acyl group, an alkylamino group and an arylamino group, or $R^4$ and $R^5$ combine together to form a condensed ring, or a group having at least one fluorine atom on the ring or in a substituent attached to the ring and being represented by the formula:

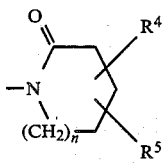

wherein n represents 1 or 2; and $R^4$ and $R^5$ are the same as the above defined $R^4$ and $R^5$, or $R^4$ and $R^5$ combine together to form a condensed ring.

7. The silver halide photographic light-sensitive material as claimed in claim 6, wherein the cyclic imido group or the 2-N-1,1-dioxo-3-(2H)-oxo-1,2-benzisothiazolyl group is substituted with a halogen atom other than a fluorine atom, a cyano group, a nitro group, an alkyl group, an aryl group, a carboxyl group, an alkoxy group, an aryloxy group, an acylamino group, a sulfonamido group, a hydroxyl group, an imido group, an alkoxycarbonyl group, an aryloxycarbonyl group, an alkylthio group, an arylthio group, an alkylsulfonyl group, an arylsulfonyl group, a carbamoyl group, a sulfamoyl group, an alkoxycarbonylamino group, an aryloxycarbonylamino group, a ureido group, an acyl group, an alkylamino group or an arylamino group.

8. The silver halide photographic light-sensitive material as claimed in claim 1, wherein the color image forming coupler is represented by the following gneeral formula (III), (IV), (V), (VI) or (VII)

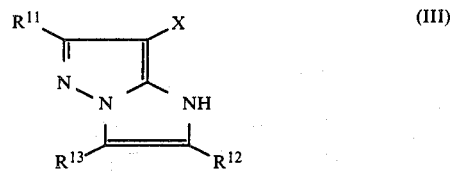

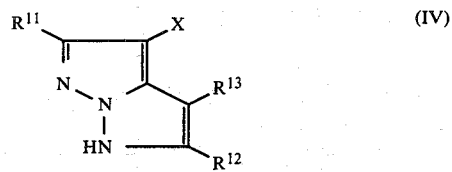

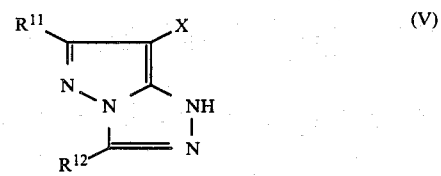

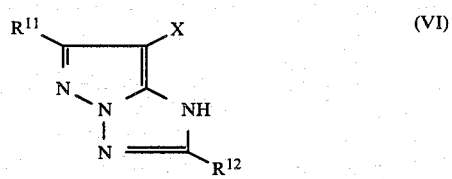

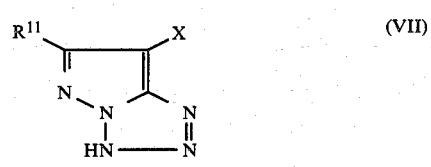

wherein $R^{11}$, $R^{12}$ and $R^{13}$ each represents a hydrogen atom, a halogen atom, an alkyl group, an aryl qroup, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group or an aryloxycarbonyl group or $R^{12}$ and $R^{13}$ in general formula (III) combine with each other to form a 5-membered, 6-membered or 7-membered non-aromatic ring or $R^{12}$ and $R^{13}$ in general formula (IV) combine with each other to form a 5-membered, 6-membered or 7-membered saturated, unsaturated or aromatic ring; and X represents the group capable of being released upon coupling and represented by general formula (II) as defined in claim 3; or $R^{11}$, $R^{12}$, $R^{13}$ or X is a divalent group to form a bis coupler.

9. The silver halide photographic light-sensitive material as claimed in claim 8, wherein the color image forming coupler is a polymer coupler in which the coupler moiety derived from the coupler represented by general formula (III), (IV), (V), (VI) or (VII) is present at the main chain or the side chain of a polymer.

10. The silver halide photographic light-sensitive material as claimed in claim 8, wherein the divalent group to form a bis coupler represented by $R^{11}$, $R^{12}$ or $R^{13}$ is a substituted or unsubstituted alkylene group, a substituted or unsubstituted phenylene group, a group of the formula $-NHCO-R^{14}-CONH-$, wherein $R^{14}$ represents a substituted or unsubstituted alkylene group or a substituted or unsubstituted phenylene group, or a group of the formula, $-S-R^{14}-S-$, wherein $R^{14}$ represents a substituted or unsubstituted alkylene group.

11. The silver halide photographic light-sensitive material as claimed in claim 8, wherein the divalent group to form a bis coupler represented by X is a divalent group derived from the monovalent group for X as defined in claim 8.

12. The silver halide photographic light-sensitive material as claimed in claim 9, wherein $R^{11}$, $R^{12}$, $R^{13}$ or X in general formula (III), (IV), (V), (VI), or (VII) represents a vinyl group or a linking group to a vinyl group.

13. The silver halide photographic light-sensitive material as claimed in claim 12, wherein the linking group represented by $R^{11}$, $R^{12}$, $R^{13}$ or X is a substituted or unsubstituted alkylene group, a substituted or unsubstituted phenylene group, $-NHCO-$, $-CONH-$, $-O-$, $-OCO-$, an aralkylene group or a combination thereof.

14. The silver halide photographic light-sensitive material as claimed in claim 12, wherein the vinyl group may further have a substituent selected from a chlorine atom and a lower alkyl group having from 1 to 4 carbon atoms in addition to the coupler moiety.

15. The silver halide photographic light-sensitive material as claimed in claim 9, wherein the polymer coupler is a homopolymer.

16. The silver halide photographic light-sensitive material as claimed in claim 9, wherein the polymer coupler is a copolymer.

17. The silver halide photographic light-sensitive material as claimed in claim 9, wherein the polymer coupler comprises a copolymer containing a repeating unit derived from a non-color forming ethylenic monomer which does not couple with the oxidation product of an aromatic primary amine developing agent.

18. The silver halide photographic light-sensitive material as claimed in claim 17, wherein the non-color forming monomer is an acrylic acid, an ester of acrylic acid, an amide of acrylic acid, a vinyl ester, an acrylonitrile, an aromatic vinyl compound, itaconic acid, citraconic acid, crotonic acid, vinylidene chloride, a vinyl alkyl ether, maleic acid, maleic anhydride, an ester of maleic acid, N-vinyl-2-pyrrolidone, N-vinyl pyridine or 2- or 4-vinyl pyridine.

19. The silver halide photographic light-sensitive material as claimed in claim 9, wherein the polymer coupler is in the form of a latex.

20. The silver halide photographic light-sensitive material as claimed in claim 8 or 9, wherein the color image forming coupler is represented by general formula (III), (IV), (VI) or (VII).

21. The silver halide photographic light-sensitive material as claimed in claim 20, wherein the color image forming coupler is represented by general formula (III) or (VI).

22. The silver halide photographic light-sensitive material as claimed in claim 1, wherein the color image forming coupler is present in an amount of from about 0.002 to 0.5 mol per mol of silver halide.

23. The silver halide photographic light-sensitive material as claimed in claim 22, wherein the color image forming coupler is present in an amount of from about 0.005 to 0.1 mol per mol of silver halide.

24. The silver halide photographic light-sensitive material as claimed in claim 1, wherein the color image forming coupler is present in a silver halide emulsion layer.

25. The silver halide photographic light-sensitive material as claimed in claim 24, wherein the silver halide emulsion layer is a green-sensitive silver halide emulsion layer.

26. The silver halide photographic light-sensitive material as claimed in claim 25, wherein the photographic light-sensitive material further comprise a blue-sensitive silver halide emulsion layer containing a yellow color image forming coupler and a red-sensitive silver halide emulsion layer containing a cyan color image forming coupler.

27. The silver halide photographic light-sensitive material as claimed in claim 1, wherein the photographic light-sensitive material has at least two silver halide emulsion layers which are sensitive to the same spectral wavelength range but have different sensitivities from each other.

28. The silver halide photographic light-sensitive material as claimed in claim 1, wherein the photographic light-sensitive material has at least three silver halide emulsion layers which are sensitive to the same spectral wavelength range but have different sensitivities from each other.

* * * * *